United States Patent
Dähne et al.

(10) Patent No.: US 11,052,035 B2
(45) Date of Patent: *Jul. 6, 2021

(54) HAIR TREATMENT METHOD AND KIT THEREOF

(71) Applicant: Noxell Corporation, Hunt Valley, MD (US)

(72) Inventors: Lars Siegfried Dähne, Berlin (DE); Mathias Kurt Herrlein, Schwalbach am Taunus (DE); Moritz Klickermann, Berlin (DE); Tatjana Schaefer, Schwalbach (DE); Stephen Robert Schofield, Egham (GB); Cagri Üzüm, Berlin (DE)

(73) Assignee: WELLA OPERATIONS US, LLC, Calabasas, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 16/096,097

(22) PCT Filed: Apr. 25, 2017

(86) PCT No.: PCT/US2017/029453
§ 371 (c)(1),
(2) Date: Oct. 24, 2018

(87) PCT Pub. No.: WO2017/189601
PCT Pub. Date: Nov. 2, 2017

(65) Prior Publication Data
US 2019/0117550 A1    Apr. 25, 2019

(30) Foreign Application Priority Data

Apr. 25, 2016 (EP) .................... 16166943

(51) Int. Cl.
*A61Q 5/08* (2006.01)
*A61K 8/84* (2006.01)
(Continued)

(52) U.S. Cl.
CPC ............. *A61K 8/84* (2013.01); *A61K 8/73* (2013.01); *A61K 8/731* (2013.01); *A61K 8/733* (2013.01);
(Continued)

(58) Field of Classification Search
None
See application file for complete search history.

(56) References Cited

U.S. PATENT DOCUMENTS

| 6,106,579 A | 8/2000 | Kunz et al. |
| 2003/0106168 A1 | 6/2003 | Tian et al. |
| 2016/0120285 A1* | 5/2016 | Crne ............ A61Q 5/065 132/208 |

FOREIGN PATENT DOCUMENTS

| DE | 10152940 A1 | 5/2003 |
| EP | 2020254 A1 | 2/2009 |

(Continued)

OTHER PUBLICATIONS

"European Application Serial No. 16166943.7, Communication Pursuant to Article 94(3) EPC dated Feb. 21, 2019", 5 pgs.
(Continued)

*Primary Examiner* — Jyothsna A Venkat
(74) *Attorney, Agent, or Firm* — Victoria Friedman; Dennemeyer & Associates, LLC

(57) ABSTRACT

Method for treating hair comprising the successive application onto hair of polymeric layers which can be removed to a large extent or even totally in an easy manner upon request of the user by using a composition having a pH less than 7.

1 Claim, 1 Drawing Sheet

(51) Int. Cl.
  *A61K 8/81* (2006.01)
  *A61K 8/73* (2006.01)
  *A61Q 5/06* (2006.01)

(52) U.S. Cl.
  CPC ............ *A61K 8/8147* (2013.01); *A61Q 5/065* (2013.01); *A61Q 5/08* (2013.01); *A45D 2200/25* (2013.01); *A61K 2800/43* (2013.01); *A61K 2800/5424* (2013.01); *A61K 2800/5426* (2013.01)

(56) References Cited

FOREIGN PATENT DOCUMENTS

| EP | 3006017 A1 | 4/2016 |
|---|---|---|
| WO | WO-2009073759 A1 | 6/2009 |
| WO | WO-2017189601 A1 | 11/2017 |

OTHER PUBLICATIONS

"International Application Serial No. PCT US2017 029453, International Preliminary Report on Patentability dated Nov. 8, 2018", 10 pgs.

"European Application Serial No. 16166943.7, Communication Pursuant to EPC Rule 69 dated Nov. 6, 2017", 2 pgs.

"European Application Serial No. 16166943.7, Extended European Search Report dated Jul. 21, 2016", 9 pgs.

"European Application Serial No. 16166943.7, Response filed May 2, 2018 to Communication Pursuant to EPC Rule 69 dated Nov. 6, 2017", w/ English Claims, 15 pgs.

"International Application Serial No. PCT/US2017/029453, International Search Report dated Jun. 21, 2017", 5 pgs.

"International Application Serial No. PCT/US2017/029453, Written Opinion dated Jun. 21, 2017", 8 pgs.

"European Application Serial No. 16166943.7, Communication Pursuant to Article 94(3) EPC dated Mar. 19, 2020", 5 pgs.

\* cited by examiner

| Example No. | Native hair | After Coating | After shampoo (comparative examples A) | Washing with pH 11.5 (comparative examples B) | Washing with pH 2 (Example) |
|---|---|---|---|---|---|
| 1 |  | 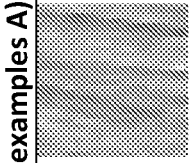 | 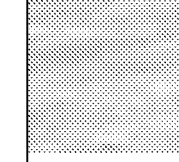 (1A) | 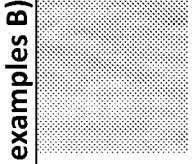 (1B) | 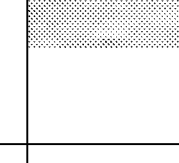 (1) |
| 2 |  | 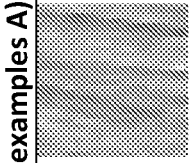 | 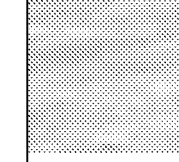 (2A) | 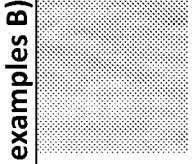 (2B) | 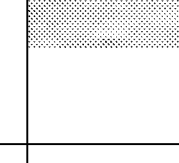 (2) |
| 3 |  | 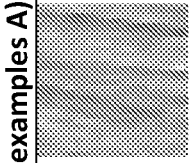 | 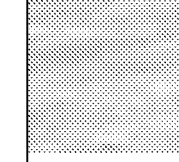 (3A) | 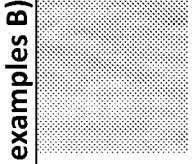 (2B) | 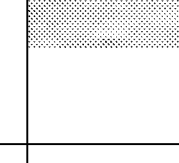 (3) |
| 4 |  | 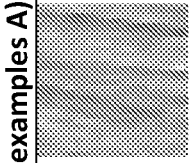 | 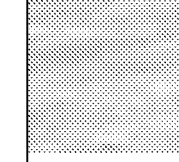 (4A) | 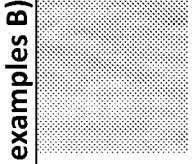 (4B) | 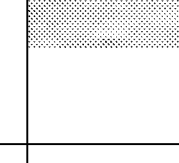 (4) |

HAIR TREATMENT METHOD AND KIT THEREOF

CROSS-REFERENCE TO RELATED APPLICATION

This application is a U.S. National Stage Filing under 35 U.S.C. 371 from international Application No. PCT/US2017/029453, filed on Apr. 25, 2017, and published as WO 2017/189601 on Nov. 2, 2017, which claims the benefit of priority to European Application No. 16166943.7, filed on Apr. 25, 2016, which applications are incorporated by reference herein in their entirety.

FIELD OF THE INVENTION

The invention is directed to a method for treating hair comprising the successive application onto hair of polymeric layers which can be removed to a large extent or even totally in an easy manner upon request of the user.

BACKGROUND OF THE INVENTION

Different methods for changing the natural colour of hair are known in the art. These methods involve the use of hair colouring compositions which allow either permanent or temporary change of hair colour. Hair colouring compositions which are used to permanently change the colour of hair, also called oxidative hair colouring compositions, typically comprise oxidative hair dye precursors, which can diffuse into the hair through the cuticle and into the cortex where they then react with each other and a suitable oxidizing agent to form the end dye molecules. Due to their larger size, the resultant molecules are unable to readily diffuse out of the hair during subsequent washing with water and/or detergents; hence delivering a consumer-desired permanency of colour. This reaction typically takes place at approximately pH 10 to 11 in the presence of an alkalizing agent and an oxidizing agent. Typically an oxidizing composition (also called developer and/or oxidizing component) comprising the oxidizing agent and a dye composition (also called tint or dye component) comprising the alkalizing agent and if present the hair dye precursors are mixed shortly before use. The consumer repeats this process regularly in order to maintain the desired hair colour, shade and intensity of colour and to ensure continual, even coverage of the hair including coverage of new hair growth. The problem with standard oxidative hair colouring methods is that the conditions under which the reaction is taking place, i.e. the high pH value as well as the presence of an oxidizing agent may cause damage to the structure of the hair and may be irritating for the scalp of the user, especially when such a process is repeated regularly and the compositions which are usually used have an undesirable odour. Furthermore, obtaining the desired colour result is not easy since standard oxidative hair colouring compositions are reactive compositions and it is therefore not easy to control the reaction on hair. Finally, once the hair has been coloured with oxidative hair colouring compositions, it is particularly difficult for the user to remove totally the colour or even to a large extent, e.g. to retrieve its natural hair colour. In order to do so, the user would typically need to either colour its hair with a new oxidative hair colouring composition or wait for the new hair to grow.

Alternatively, methods for temporarily changing the colour of hair have also been developed. These methods usually involve the application of hair colouring compositions comprising direct dyes. Direct dye compositions are usually less aggressive for the hair since they are non reactive compositions. However, since direct dyes are low molecular weight molecules, they may have the tendency to also colour the scalp of the user. Even if the hair colouration which is obtained is typically characterized by a weaker washfastness than when the hair is coloured with standard oxidative hair colouring compositions, i.e. the colouration is typically fading after regular washing of the hair with standard shampoo compositions, it may still be difficult or at least requires a lot of time for the user to remove the colour at least to a large extent, if not entirely.

Methods for temporarily changing the colour of hair involving the application of hair colouring compositions comprising polymeric dyes have also been developed. The hair colouration which is obtained by application of polymeric dyes onto hair is also typically characterized by a weaker washfastness than when the hair is coloured with standard oxidative hair colouring compositions. However, it may also be difficult or at least require a lot of time for the user to remove the colour at least to a large extent, if not entirely.

Therefore, there is still the need for a method for treating hair which makes easier the removal upon request of the user of an artificial colouration which is obtained thereafter on hair. This method should preferably involve the use of compositions which are less aggressive for the hair and for the scalp. Finally, this method should also preferably involve the use of low odour compositions.

The inventors have surprisingly found that at least some of these needs may be met by the method for treating hair according to the present invention, wherein a polymeric layer is obtained onto the hair by successively applying a cationic polymer and an anionic polymer prior to colouring the hair and wherein a portion of this polymeric layer and therefore any artificial colouration that is obtained thereafter on hair can be removed upon request of the user by using a composition having a certain pH.

SUMMARY OF THE INVENTION

The present invention relates to a method for treating hair comprising:

A) carrying out the following sequence of steps:

i) applying a first composition comprising one or more first cationic polymer(s) to a first portion of the hair; and ii) applying a second composition comprising one or more first anionic polymer(s) to a second portion of the hair; and B) applying a third composition having a pH of less than 7 to a third portion of hair, wherein the first, second and third portions have at least one first common area and wherein the first anionic polymer(s) are weak anionic polymers.

The present invention also relates to a kit for treating hair comprising a first component comprising the first composition as defined hereinbefore, a second component comprising the second composition as defined hereinbefore and a third component comprising the third composition as defined hereinbefore. The present invention also pertains to the use of a composition for decolouration of hair.

BRIEF DESCRIPTION OF THE DRAWINGS

FIG. 1 illustrates the experimental results of a removal of a coloured polymer system from hair according to embodiments.

DETAILED DESCRIPTION OF THE INVENTION

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All ratios or percentages are weight ratios or weight percentages unless specifically stated otherwise.

By "cationic polymer" it is meant any polymer comprising an overall charge at full protonation which is positive.

By "cationic coloured polymer" it is meant any cationic polymer comprising at least one chromophore and/or at least one fluorophore either in the skeleton or as pendent group.

By "cationic uncoloured polymer" it is meant any cationic polymer which does not comprise any chromophore or fluorophore either in the skeleton or as pendent group.

By "anionic polymer" it is meant any polymer comprising an overall charge at full deprotonation which is negative.

By "anionic coloured polymer" it is meant any anionic polymer comprising at least one chromophore and/or at least one fluorophore either in the skeleton or as pendent group.

By "anionic uncoloured polymer" it is meant any anionic polymer which does not comprise any chromophore or fluorophore either in the skeleton or as pendent group.

By "full protonation" it is meant the state at which the different protonable groups of a polymer are all fully protonated.

By "full deprotonation" it is meant the state at which the different deprotonable groups of a polymer are all fully deprotonated.

By "weak anionic polymer" it is meant an anionic polymer whose charge is dependent on the pH when solubilized in water. According to an embodiment, the weak anionic polymer may have a pKa value in a range of 2 to 8, particularly in a range of 3 to 7, more particularly in a range of 3.5 to 7, and further particularly in a range of 4 to 7. According to further embodiments, the weak anionic polymer may have a pKa value in a range of 3.5 to 6.5, and further particularly between 4 and 6.

Method for Treating Hair

The present invention relates to a method for treating hair as stated hereinbefore.

Having at least one common area between the first portion of the hair to which the first composition is applied and the second portion of the hair to which the second composition is applied ensures that at least a portion of the second composition is applied to the same portion of the hair as at least a portion of the first composition. In this portion of the hair a polymeric layer made of an anionic polymeric sublayer positioned on top of a cationic polymeric sublayer is obtained after the successive application of the first cationic polymer(s) and the first anionic polymer(s). This polymeric layer is hereinafter referred to as the first polymeric layer.

Hair is naturally negatively charged. Therefore, the inner sublayer of the coated hair which is positively charged can easily attach to the surface of the hair and the outer sublayer of the coated hair which is negatively charged can easily attach to the surface of the cationic polymeric sublayer positioned underneath. Since the outer sublayer of the coated hair has an electrostatic structure similar to the one of the outer layer of natural hair, it is possible to apply any further hair treatment on top of the first polymeric layer that would usually be directly applied onto hair.

While not wishing to be bound by theory, it is believed that having at least one common area between the first portion of the hair to which the first composition is applied and the second portion of the hair to which the second composition is applied and the third portion of the hair to which the third composition is applied, ensures that the third composition having a low pH enters into contact with the first polymeric layer and therefore helps to remove at least a part of the first polymeric layer and therefore any layer, e.g. a coloured layer which can be obtained on top of the first polymeric layer during a subsequent step.

Therefore, the method according to the present invention is particularly advantageous since it is a simple way for treating the hair to make easier the removal of any artificial colouration that is obtained thereafter on hair. Furthermore, the compositions which are used in the method according to the present invention are particularly advantageous since these compositions exhibit low odour.

First Composition

The first composition may be applied all over the hair.

The first composition may be applied in one go or step-by-step to the hair. The first composition may be applied step-by-step, for example in case the hair is damaged. Applying the first composition step-by-step, may help to ensure that the hair is saturated with the first composition and may therefore provide a better coverage of the hair with the first composition.

First Cationic Polymer(s)

The first composition comprises one or more first cationic polymer(s).

The first cationic polymer(s) may be weak cationic polymer(s), or may be strong cationic polymer(s). According to an embodiment, the weak cationic polymer may have a pKa value in a range from 5 to 10, particularly from 6 to 10, and more particularly from 7 to 10, further particularly between 7.5 and 10, and even more particularly between 8 and 10. According to further embodiments, the weak cationic polymer may have a pKa value in a range from 8 to 9.5.

The first cationic polymer(s) may be coloured.

The first cationic polymer(s) may preferably be uncoloured.

The first cationic polymer(s) may comprise one or more amino functional group(s) per polymer chain, wherein the amino functional group(s) are selected from the group consisting of primary, secondary, tertiary amino functional groups and mixtures thereof.

The first cationic polymer(s) may be selected from the group consisting of polyethyleneimine, polyallylamine hydrochloride, polyvinylamine, copolymers thereof and mixtures thereof.

The first cationic polymer(s) may preferably be selected from the group consisting of polyethyleneimine, copolymers thereof and mixtures thereof.

The copolymers may be random or block copolymers.

The first cationic polymer(s) may be linear or branched.

The first cationic polymer(s) may be selected from the group consisting of:

a) Linear polyethyleneimine of the formula:

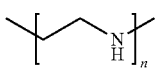

in which n is an integer representing the degree of polymerization, wherein n ranges from 50 to 20,000, alternatively from 100 to 3,500;
b) Branched polyethyleneimine consisting of primary, secondary and tertiary amine groups of the formula:

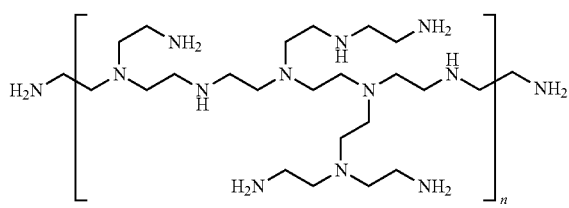

in which n is an integer representing the degree of polymerization, wherein n ranges from 5 to 4,000, alternatively from 50 to 500;
c) Polyallylamine hydrochloride of the formula:

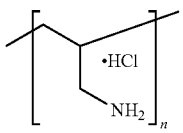

in which n is an integer representing the degree of polymerization, wherein n ranges from 50 to 20,000, alternatively from 150 to 2000; and
d) copolymers thereof and mixtures thereof.

The copolymers may be random or block copolymers.

The first cationic polymer(s) may have a charge density at full protonation of at least 0.3, preferably at least 0.6, more preferably at least 0.8, even more preferably at least 1.0 positive charges per monomer unit.

The first cationic polymer(s) may have a weight average molecular weight of more than 0.5 kD, preferably from 0.5 kD to 5000 kD, more preferably from 2 kD to 1000 kD, even more preferably from 10 kD to 200 kD, most preferably from 25 kD to 70 kD.

Second Composition

The second composition may be applied all over the hair.

The second composition is applied after the first composition to the hair.

The second composition may be applied in one go or step-by-step to the hair. The second composition may be applied step-by-step, for example in case the hair is damaged. Applying the second composition step-by-step, may help to ensure that the hair is saturated with the second composition and may therefore provide a better coverage of the hair with the second composition.

First Anionic Polymer(s)

The second composition comprises one or more first anionic polymer(s). The first anionic polymer(s) may be weak anionic polymer(s).

The first anionic polymer(s) may be coloured.

The first anionic polymer(s) may preferably be uncoloured.

The first anionic polymer(s) may comprise one or more functional group(s) per polymer chain selected from the group consisting of phenyl groups, alkyl groups comprising at least 8 carbon atoms and mixtures thereof.

The first anionic polymer(s) may be selected from the group consisting of poly(acrylic acid) salts, poly(methacrylic acid) salts, alginic acid salts, carboxymethylcellulose salts, carboxydextrane salts, copolymers thereof and mixtures thereof.

The copolymers may be random or block copolymers.

The first anionic polymer(s) may be linear or branched.

The first anionic polymers may be selected from the group consisting of:
a) Polyacrylic acid (PAA) of the formula:

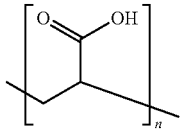

in which n is an integer representing the degree of polymerization, wherein n ranges from 50 to 20,000, alternatively from 150 to 1,000;
b) Alginic acid sodium salt;
c) Carboxymethylcellulose sodium salt of the formula:

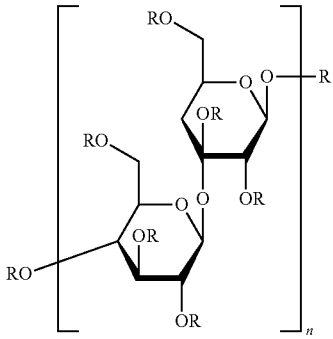

in which:
R is H or $(CH_2)_2COONa$ and
n is an integer representing the degree of polymerization; and
d) copolymers thereof and mixtures thereof.

The copolymers may be random or block copolymers.

The first anionic polymer(s) may have a charge density at full deprotonation of at least 0.3, alternatively at least 0.6, alternatively at least 0.8, alternatively at least 1.0 negative charges per monomer unit.

The first anionic polymer(s) may have a weight average molecular weight of at least 1 kD, alternatively from 10 kD to 1000 kD, alternatively from 70 to 500 kD.

First and Second Compositions

The first cationic polymer(s) and the first anionic polymer(s) may preferably be uncoloured. The first and the second portions of the hair may be the same. The first and the second compositions may be applied all over the hair. Step A) may be repeated at least once prior to step B).

Third Composition

The third composition may be applied all over the hair.

Step B) is carried out after step A). Step B) may be carried out immediately after step A) or at least 1 hour after step A)

or at least 24 hours after step A) or at least 10 days after step A) or at least one month after step A).

The third composition may have a pH of less than 7. The third composition may have a pH ranging from 1 to 7, particularly from 1 to 6, further particularly from 1 to 5.5, more particularly from 2 to 6, even more particularly from 1.5 to 5, and further more particularly from 1.5 to 4.5.

The third composition may be selected from the group consisting of an aqueous solution, an oil-in-water emulsion and a water-in-oil emulsion. The third composition may preferably be an aqueous solution. In the embodiments wherein the third composition is an oil-in-water emulsion or a water-in-oil emulsion, the pH of the third composition corresponds to the pH of the aqueous phase.

While not wishing to be bound by theory, it is believed that the low pH of the third composition may help to lower the overall charge of the first anionic polymer(s) and weaken the interaction between the first anionic polymer(s) and the first cationic polymer(s) inside the first polymeric layer and therefore may help to remove a part of the first polymeric layer, i.e. a part of the anionic polymeric sublayer and/or cationic polymeric sublayer. While not wishing to be bound by theory, it is also believed that the low pH of the third composition may help to lower the overall charge of the first anionic polymer(s) and also weaken the interaction between the first anionic polymer(s) and any cationic polymer(s) on the first anionic polymer(s).

The pH value of the third composition may be selected relative to the pKa value of the weak anionic polymer(s). According to an embodiment, the difference between the pH value of the third composition and the pKa value of the weak anionic polymer(s) is at least 1, particularly at least 1.5, more particularly at least 2, and even more particularly at least 2.5. The pH value of the third composition can therefore be lower than the pKa value of the weak anionic polymer at least by 1, particularly by 1.5, more particularly by 2, and even more particularly by 2.5. Having a given difference between the pH value of the third composition and the pKa value of the weak anionic polymer(s) ensures that the weak anionic polymer(s) is/are sufficiently discharged.

The third composition may have a pH of less than 7, particularly less than 6, more particularly less than 5.5, even more particularly less than 5, and further more particularly less than 4.5 or even less than 4, and may comprise at least one of: one or more anionic surfactant(s); one or more oxidizing agent(s); one reducing agent(s). The third composition may also include other surfactants such as amphoteric surfactants, cationic surfactants and non-ionic surfactants.

pH Modifier and/or Buffering Agent

The third composition may comprise at least one pH modifier and/or buffering agent selected from the group consisting of ammonia, alkanolamines, guanidinium salts, alkali metal hydroxides, alkali metal carbonates, ammonium hydroxides, ammonium carbonates, inorganic acids, organic acids and mixtures thereof. The pH modifier and/or buffering agent may preferably be selected from the group consisting of alkanolamines, guanidinium salts, alkali metal hydroxides, alkali metal carbonates, inorganic acids, organic acids and mixtures thereof.

The alkanolamines may be selected from the group consisting of monoethanolamine, diethanolamine, triethanolamine, monopropanolamine, dipropanolamine, tripropanolamine, 2-amino-2-methyl-1-propanol, 2-amino-2-hydroxymethyl-1,3,-propandiol and mixtures thereof.

The inorganic or organic acids may be selected from the group consisting of phosphoric acid, acetic acid, ascorbic acid, citric acid or tartaric acid, hydrochloric acid and mixtures thereof.

Cationic Surfactant(s)

The third composition may comprise one or more cationic surfactant(s). The cationic surfactant(s) may preferably comprise one or more linear or branched group(s) comprising at least 8 carbon atoms. The cationic surfactant(s) may more preferably comprise one or more linear or branched group(s) comprising from 8 to 22 carbon atoms. The cationic surfactant(s) may even more preferably comprise one or more linear or branched group(s) comprising from 10 to 22 carbon atoms. The cationic surfactant(s) may most preferably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

While not wishing to be bound by theory, it is believed that the interaction between the cationic surfactant(s) comprised in the third composition and the first anionic polymer(s) may be stronger than the interaction between the first anionic polymer(s) and the first cationic polymer(s) inside the first polymeric layer and therefore may help to remove a part of the first polymeric layer, i.e. a part of the anionic polymeric sublayer.

While not wishing to be bound by theory, it is believed that the interaction between the cationic surfactant(s) comprised in the third composition and the first anionic polymer(s) may be even stronger when the first anionic polymer(s) are more hydrophobic, e.g. when the first anionic polymer(s) comprise one or more functional group(s) per polymer chain selected from the group consisting of phenyl group, alkyl groups comprising at least 8 carbon atoms and mixtures thereof.

The cationic surfactant(s) may be selected from the group consisting of quaternary ammonium salts, amido-amines, primary amines, secondary amines, tertiary amines and mixtures thereof.

The cationic surfactant(s) may be selected from quaternary ammonium salts having the following formula:

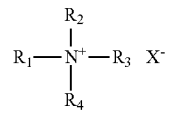

wherein:
$R_1$ is selected from the group consisting of linear or branched groups optionally comprising at least one heteroatom selected from oxygen, nitrogen, sulfur and halogens, wherein the linear or branched groups comprise from 6 to 22 carbon atoms, preferably from 16 to 22 carbon atoms; and $R_2$ is selected from the group consisting of linear or branched groups optionally comprising at least one heteroatom selected from oxygen, nitrogen, sulfur and halogens, wherein the linear or branched groups comprise from 1 to 22 carbon atoms, preferably from 16 to 22 carbon atoms, aryl groups and alkylaryl groups; and $R_3$ and $R_4$ are independently selected from the group consisting of linear or branched groups comprising from 1 to 4 carbon atoms, aryl groups and alkylaryl groups; and X is an anion selected from chloride, bromide, iodide, alkyl sulfates, phosphates, alkyl sulfonates, alkylaryl sulfonates and anions derived from organic acids or amino acids.

The linear or branched groups may be aliphatic groups. The aliphatic groups may be selected from alkyl, alkoxy and alkylamide groups.

The amino acid may be glutamic acid. The anions derived from organic acids may be acetate anions or lactates anions.

The cationic surfactant(s) may be selected from amidoamines having the following formula:

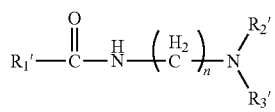

wherein:
R$_1$' is selected from the group consisting of linear or branched groups optionally comprising at least one heteroatom selected from oxygen, nitrogen, sulfur and halogens, wherein the linear or branched groups comprise from 10 to 22 carbon atoms, preferably from 16 to 22 carbon atoms;

R'$_2$ and R'$_3$ are independently selected from the group consisting of hydrogen, linear or branched groups optionally comprising at least one heteroatom selected from oxygen, nitrogen, sulfur and halogens, wherein the linear or branched groups comprise from 1 to 4 carbon atoms, aryl groups and alkylaryl groups;

n is integer ranging from 1 to 4.

The linear or branched groups may be aliphatic groups. The aliphatic groups may be selected from alkyl, alkoxy and alkylamide groups.

The cationic surfactant(s) may be selected from the group consisting of cetrimonium halide, stearimonium halide, behentrimonium halide, behentrimonium halide, stearamidopropyltrimonium halide, dodecyltrimethylammonium halide, didodecyldimethylammonium halide, tetradecyltrimethylammonium halide, distearyldimethylammonium halide, dicetyldimethylammonium halide, distearoylethyl dimonium halide, behenamidopropyltrimonium methosulfate, behenamidopropyl dimethylamine, stearamidopropyl dimethylamine, behenamidopropyl diethylamine, behenamidoethyl diethylamine, behenamidoethyl dimethylamine, arachidamidopropyl dimethylamine, arachidamidopropyl diethylamine, arachidamidoethyl diethylamine, arachidamidoethyl dimethylamine, and mixtures thereof, wherein the halide is selected from bromide and chloride. The cationic surfactant(s) may preferably be selected from the group consisting of dodecyltrimethylammonium halide, didodecyldimethylammonium halide, tetradecyltrimethylammonium halide, cetrimonium halide and mixtures thereof, wherein the halide is selected from bromide and chloride.

The third composition comprises a total amount of cationic surfactants ranging from 0.01% to 10%, preferably from 0.05% to 5%, more preferably from 0.3% to 3% by total weight of the third composition. The amount of each particular cationic surfactant or mixtures thereof described hereinbefore can account for up to 100% (or 100%) of the total amount of cationic surfactants in the third composition.

Amphoteric Surfactant(s)

The third composition may comprise one or more amphoteric surfactant(s). The amphoteric surfactant(s) may preferably comprise one or more linear or branched group(s) comprising at least 8 carbon atoms. The amphoteric surfactant(s) may more preferably comprise one or more linear or branched group(s) comprising from 8 to 40 carbon atoms. The amphoteric surfactant(s) may even more preferably comprise one or more linear or branched group(s) comprising from 10 to 40 carbon atoms. The amphoteric surfactant(s) may most preferably comprise one or more linear or branched group(s) comprising from 16 to 35 carbon atoms. The linear or branched group(s) may optionally comprise at least one heteroatom selected from oxygen, nitrogen, sulfur and halogens. The linear or branched groups may be aliphatic groups.

Amphoteric (zwitterionic) surfactants have both cationic and anionic centers attached to the same molecule. The cationic part may be based on primary, secondary, tertiary amines or quaternary ammonium cations. The anionic part can be more variable and may include sulfonates, as in the sultaines CHAPS (3-[(3-Cholamidopropyl)dimethylammonio]-1-propanesulfonate) and cocamidopropyl hydroxysultaine.

Suitable amphoteric surfactants may include betaines, such as cocamidopropyl betaine, phospholipids, such as phosphatidylserine, phosphatidylethanolamine, phosphatidylcholine, and sphingomyelins.

Suitable betaines may have the following formula

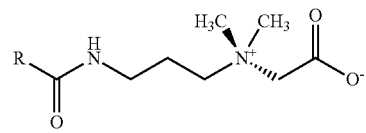

with R=alkyl chain with 5 to 21 C atoms.

Further suitable amphoteric surfactants may include sultaines which may have the following formula

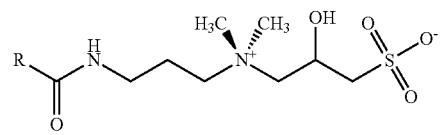

with R=alkyl chain with 5 to 21 C atoms.

Further suitable amphoteric surfactants may include taurin (2-aminoethansulfonic acid), cocoamidopropyl hydroxysultain, N-coco 3-aminopropionic acid, (or the sodium salt thereof), N-tallow 3-iminodipropionate (or the disodium salt thereof), N-carboxymethyl N-dimethyl N-9 octadecenyl ammonium hydroxide, N-cocoamidethyl N-hydroxyethylglycine, cocoamphocarboxyglycinate, cocamidopropyl betaine, and sulfobetaine.

Most preferred amphoteric surfactants are selected from the group consisting of betain, sultaines, phospholipids, aminopropionates, aminoglycinates, amphoacetate, amphodiacetate, amphopropionate, amphohydroxypropylsulfonates, and combinations thereof. Most preferred are betains selected from the group consisting of Cocamidopropyl betaine, Laurylamidopropyl betaine Tetradecyl betaine, Alkylaminopropyl betaine, Octyl betain, Cetyl betain, Staeryl betain. Amino acid Further suitable amphoteric surfactants may comprise amino acids. Specifically, amino acids with their polyampholytic character in the third composition can help to enhance the ionic and hydrophobic interactions between the hair surface. Suitable amino acids may be selected from the group consisting of alanine, arginine, asparagine, aspartic acid, cysteine, glutamic acid, glutamine, glycine, proline, selenocysteine, serine, tyrosine, histidine, isoleucine, leucine, lysine, methionine, phenylalanine, threonine, tryptophan, valine, and combinations thereof.

According to an embodiment, the third composition may comprise one or more anionic surfactant(s). The anionic surfactant(s) may include, for example, sodium dodecyl sulfate SDS, sodium xylenesulfonat sodium naphthalenesulfonate, dodecyl trimethyl ammonium bromid, sodium lauryl sulfate SDS, Tween 20.

Nonionic Surfactant(s)

The third composition may comprise one or more nonionic surfactant(s). The nonionic surfactant(s) may preferably comprise one or more linear or branched group(s) comprising at least 8 carbon atoms. The nonionic surfactant(s) may more preferably comprise one or more linear or branched group(s) comprising from 8 to 22 carbon atoms. The nonionic surfactant(s) may even more preferably comprise one or more linear or branched group(s) comprising from 10 to 22 carbon atoms. The nonionic surfactant(s) may most preferably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

The nonionic surfactants may be selected form the group consisting of alkohols, ethers, esthers, alkanolamides and aminoxides.

Suitable alcohols may include primary alcohols ranging from 8 to 18 carbon atoms. Preferred primary alcohols are fatty alcohols, cetyl alcohol, stearyl alcohol, cetostearyl alcohol (consisting predominantly of cetyl and stearyl alcohols), and oleyl alcohol.

Suitable ethers may include Polyoxyethylene glycol alkyl ethers (Brij) (CH3-(CH2)10-16-(O—C2H4)1-25-OH), Octaethylene glycol monododecyl ether, Pentaethylene glycol monododecyl ether, Polyoxypropylene glycol alkyl ethers (CH3-(CH2)10-16-(O—C3H6)1-25-OH), Glucoside alkyl ethers (CH3-(CH2)10-16-(O-Glucoside)1-3-OH), Decyl glucoside, Lauryl glucoside, Octyl glucoside, Polyoxyethylene glycol octylphenol ethers (C8H17-(C6H4)-(O—C2H4)1-25-OH, Triton X-100), Polyoxyethylene glycol alkylphenol ethers (C9H19-(C6H4)-(O—C2H4)1-25-OH, Nonoxynol-9), and block copolymers of polyethylene glycol and polypropylene glycol (Poloxamers).

Suitable esthers may include Glycerol alkyl esters, such as Glyceryl laurate, Polyoxyethylene glycol sorbitan alkyl esters, such as Polysorbate, and Sorbitan alkyl esters, such as Spans.

Suitable alkanolamides may include cocamide MEA, cocamide DEA

Suitable aminoxides may include Dodecyldimethylamine oxide and Polyethoxylated tallow amine (POEA).

Anionic Surfactant(s)

The third composition may comprise one or more anionic surfactant(s). The anionic surfactant(s) may preferably comprise one or more linear or branched group(s) comprising at least 8 carbon atoms. The anionic surfactant(s) may more preferably comprise one or more linear or branched group(s) comprising from 8 to 22 carbon atoms. The anionic surfactant(s) may even more preferably comprise one or more linear or branched group(s) comprising from 10 to 22 carbon atoms. The anionic surfactant(s) may most preferably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

Suitable anionic surfactant(s) may comprise at least one anionic functional groups at their head selected from sulfate, sulfonate, phosphate and carboxylates.

Suitable alkyl sulfates include ammonium lauryl sulfate, sodium lauryl sulfate (sodium dodecyl sulfate, SLS, or SDS), and alkyl-ether sulfates, such as sodium laureth sulfate (sodium lauryl ether sulfate or SLES), and sodium myreth sulfate.

Further suitable anionic surfactants may include Docusate (dioctyl sodium sulfosuccinate), alkyl-aryl ether phosphate, alkyl ether phosphate, alkyl carboxylate, such as sodium stearate, sodium lauroyl sarcosinate, ammonium laureth sulfate, disodium lauryl sulfosuccinate, and sodium lauryl sulphoacetate.

Preferred anionic surfactants are selected from the group consisting of sodium laurylethersulfate, sodium laurethethersulfate, sodium dodecyl sulfate, ammonium laurethethersulfat, ammonium dodecyl sulfate, alkylbenzenesulfonate, and combinations thereof.

Oxidizing Agent(s)

The third composition may comprise one or more oxidizing agent(s). The oxidizing agent(s) may preferably be selected from the group consisting of hypochlorous acid, peracetic acid, persulfate, chlorine dioxide, perboric acid, salts thereof, ozone, hydrogen peroxide and mixtures thereof. The oxidizing agent(s) may more preferably be selected from the group consisting of hypochlorous acid, salts thereof and mixtures thereof. The oxidizing agent(s) may even more preferably be selected from the group consisting of sodium hypochlorite, calcium hypochlorite, potassium hypochlorite and mixtures thereof.

While not wishing to be bound by theory, it is believed that the oxidizing agent(s) comprised in the third composition may help to remove a part of the first polymeric layer.

The third composition may comprise a total amount of oxidizing agents selected from the group consisting of sodium hypochlorite, calcium hypochlorite, potassium hypochlorite and mixtures thereof of up to 25% by total weight of the third composition. The third composition may comprise a total amount of oxidizing agents selected from the group consisting of sodium hypochlorite, calcium hypochlorite, potassium hypochlorite and mixtures thereof ranging from 0.01% to 10%, preferably from 0.2% to 2%, more preferably from 0.5% to 1.5% by total weight of the third composition. The amount of each particular oxidizing agent or mixtures thereof described hereinbefore can account for up to 100% (or 100%) of the total amount of oxidizing agents in the third composition.

The third composition may be a shampoo composition, a hair conditioning composition or a hair treatment composition.

The third composition of the present invention may comprise at least one oxidizing agent and/or at least one source of an oxidizing agent. The oxidizing agents may be provided in aqueous solution or as a powder which is dissolved prior to use. Preferred oxidizing agents are water-soluble peroxygen oxidizing agents. As used herein, "water-soluble" means that in standard conditions at least 0.1 g, preferably about 1 g, more preferably 10 g of the oxidizing agent can be dissolved in 1 litre of deionized water at 25° C. Suitable water-soluble oxidizing agents include, but are not limited to: inorganic peroxygen materials capable of yielding hydrogen peroxide in an aqueous solution.

The oxidizing agents are valuable for the initial solubilisation and decolourisation of the melanin (bleaching) as well as for the activation of the hair surface such that through oxidization of proteins located at the hair surface, the overall negative charge is increased. An increased overall negative charge of the hair surface is desirable for a better attachment of the cationic polymer comprised in the hair colouring system applied to the hair in the subsequent step c) of the method of the present invention.

According to an embodiment, the third composition may comprise a total amount of oxidizing agents ranging from 0.1% to 15%, alternatively from 0.2% to 15%, alternatively from 0.3% to 15%, alternatively ranging from 0.1% to 12%, alternatively from 0.2% to 12%, alternatively from 0.3% to 12%, alternatively from 0.1% to 7%, alternatively from 0.2% to 7%, alternatively from 0.3% to 7%, alternatively from 1% to 7%, alternatively from 0.1% to 5%, alternatively from 0.2% to 5%, alternatively from 0.3% to 5%, alternatively from 0.5% to 5%, alternatively from 1% to 5%, alternatively from 2% to 5%, by total weight of the third composition. Alternatively, the third composition may comprise a total amount of oxidizing agents of less than 3%, alternatively less than 2%, alternatively less than 1%, alternatively less than 0.5%, alternatively less than 0.3% alternatively less than 0.1% by total weight of the third composition. The lower limit for the oxidizing agents may be at least 0.01% by total weight of the third composition. The third composition having a low amount of oxidizing agents is less damaging the hair than standard hair colouring composition which usually comprise a high concentration of oxidizing agent.

The third composition may also be substantially free of oxidizing agents, i.e. having oxidizing agents less than 0.1%, and more particularly less than 0.01% by total weight of the third composition. For example, a third composition having surfactants such as amphoteric surfactants may be substantially free of oxidizing agents. A third composition which comprises oxidizing agents, however, may also include surfactants such as at least one of anionic surfactants, cationic surfactants, amphoteric surfactants, non-ionic surfactants, and combination thereof.

Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired.

The third composition may comprise a water-soluble oxidizing agent selected from the group consisting of peroxides, percarbonates (which may be used to provide a source of both oxidizing agent and carbonate ions and or ammonium ions), persulphates, and mixtures thereof. The particularly preferred oxidizing agent is hydrogen peroxide.

When the third composition of the present invention is obtained by mixing a developer composition and a tint composition prior to use, the oxidizing agent may be present in the developer composition. The developer composition may be based on any desired formulation chassis, including any commercial product, for example an oil-in-water emulsion. Typical developer compositions comprise about 6% or about 9% of the H2O2 relative to the total weight of the developer composition. A preferred example of a developer composition with respectively about 6% and about 9% H2O2, comprises as INCI ingredients: Water, H2O2, Cetearyl Alcohol, Ceteareth-25, Salicylic Acid, Phosphoric Acid, Disodium Phosphate, Etidronic Acid. Another preferred example a developer composition comprises as INCI ingredients: Water, H2O2, cetearyl alcohol, lanolin alcohol, sodium lauryl sulfate, parfum, salicylic acid, phosphoric acid, disodium phosphate, linalool, hexyl cinnamal, etidronic acid, tocopherol. Another preferred example a developer composition comprises as INCI ingredients: Water, H2O2, cetearyl alchohol, lanolin alcohol, sodium lauryl sulfate, parfum, salicylic acid, phosphoric acid, disodium phosphate, linalool, hexyl cinnamal, etidronic acid, tocopherol.

Reducing Agent(s)

The third composition of the present invention may comprise at least one reducing agent and/or at least one source of a reducing agent. The reducing agents may be provided in aqueous solution or as a powder which is dissolved prior to use. The third composition may comprise a total amount of reducing agents ranging from 0.1% to 15%, alternatively from 0.2% to 15%, alternatively from 0.3% to 15%, alternatively from 0.1% to 12%, alternatively from 0.2% to 12%, alternatively from 0.3% to 12%, alternatively from 0.1% to 7%, alternatively from 0.2% to 7%, alternatively from 0.3% to 7%, alternatively from 1% to 7%, alternatively from 0.1% to 5%, alternatively from 0.2% to 5%, alternatively from 0.3% to 5%, alternatively from 0.5% to 5%, alternatively from 1% to 5%, alternatively from 2% to 5%, by total weight of the third composition.

The reducing agent(s) may preferably be selected from the group consisting inorganic reducing agent(s) and organic reducing agent(s), and combinations thereof.

Inorganic Reducing Agents:

sulfide, disulfite, thiosulfate, sulfite, phosphonic acid, hydrazine, borohydride, aluminiumhydride, hydrogen, sodium sulfite, sodium bisulfite, sodium hydrogensulfite, sodiumthiosulfate, and combinations thereof.

Organic Reducing Agents:

formic acid, ketoglutarate, DTT red, NADH/H+, dihydrolipoic acid, cysteine, vitamin C, vitamin E, Dithiothreitol (DTT), mercaptanes, thioglycolic acid, ammonium thioglycolate, sodium thioglycolate cysteine, ascorbic acid, glyceryl monothiopropionate, ammonium thiolactate, dithioerythritol, glutathione, 1,3-dithiopropanol, thioglycolamide, glyceryl monothioglycolate, glyceryl thiolactate, and combinations thereof.

The third composition may include either reducing agent(s) or oxidizing agent(s).

Alternatively, the third composition may also be substantially free of reducing agents, i.e. having reducing agents less than 0.1%, and more particularly less than 0.01% by total weight of the third composition. For example, a third composition having surfactants such as amphoteric surfactants may be substantially free of reducing agents. A third composition which comprises reducing agents, however, may also include surfactants such as at least one of anionic surfactants, cationic surfactants, amphoteric surfactants, non-ionic surfactants, and combination thereof.

Preferred reducing agents are thioglycolic acid, mercaptanes, ammonium thioglycolate, sodium thioglycolate cysteine, sodium sulfite, ascorbic acid, glyceryl monothiopropionate, ammonium thiolactate, dithiothreitol, dithioerythritol, glutathione, dihydrolipoic acid, 1,3-dithiopropanol, thioglycolamide, glyceryl monothioglycolate, sodium bisulfite, sodium hydrogensulfite, sodiumthiosulfate, glyceryl thiolactate, and combinations thereof.

First, Second and Third Compositions

The first, the second and the third portions of the hair may be the same. The first, the second and the third compositions may be applied all over the hair.

Additional Steps

Removal of the Excess of the Compositions

At least one of steps i), ii) or B), preferably all the steps i), ii) and B) may further comprise the subsequent sub-step of removing the excess of the respective composition(s) with fingers and/or a towel.

Application of Energy

Steps i) and/or ii) may further comprise the subsequent sub-step of applying energy to the hair in the form of heat, ultrasounds, infrared and/or microwaves. This sub-step may be carried out either after the application of the first or second composition to the hair or after removing the excess of the first composition or the second composition from the hair. While not wishing to be bound by theory, it is believed that applying energy to the hair may accelerate the speed of formation of the polymeric sublayers on the hair and therefore may increase the stability of the sublayers once they are formed on the hair. The hair may be heated to a temperature ranging from 5° C. to 70° C., alternatively 20° C. to 60° C., alternatively 40° C. to 60° C.

Washing and/or Rinsing

At least one of steps i), ii) or B), preferably all the steps i), ii) or B) may further comprise the subsequent sub-step of washing and/or rinsing the hair, preferably with a liquid selected from the group consisting of a cosmetically acceptable solvent, a solution comprising a cosmetically acceptable solvent and a cosmetically acceptable salt, a shampoo composition and mixtures thereof, more preferably with water.

Pre-Treatment

The hair may be pretreated prior to step i) to modify the number of positive or negative charges in some portions of the hair or all over the hair. This pretreatment may be done using chemical or physical means such as pH change, oxidation, reduction, bleaching, plasma treatment, ozone treatment, electrowetting, dry or wet ion-treatment.

Hair Colouring Step

The method according to the present invention may further comprise the step of colouring the hair by applying hair colouring composition(s). The hair colouring composition(s) may comprise coloured polymer(s) or pigment(s). The hair colouring composition(s) may form coloured layer(s) after application onto the hair.

The method may further comprise between steps A) and B) step a) of applying a fourth composition comprising one or more second cationic polymer(s) and/or at least one pigment, preferably at least one second cationic polymer to a fourth portion of the hair, wherein the fourth portion of the hair has at least one common area with the first common area and the second cationic polymer(s) are cationic coloured polymers.

Having at least one common area between the fourth portion of the hair to which the fourth composition is applied and the first common area defined hereinbefore ensures that the fourth composition is applied to the same portion of the hair wherein the first polymeric layer is obtained after the successive application of the first cationic polymer(s) and the first anionic polymer(s). While not wishing to be bound by theory it is believed that this also ensures that the third composition is also applied to the portion of the hair comprising the first polymeric layer and the coloured layer on top of it and therefore helps to remove at least a part of the first polymeric layer and at least the part of the coloured layer which is obtained on top of the part of the first polymeric layer that is removed. While not wishing to be bound by theory, it is believed that the part of the first polymeric layer that is removed is a part of the anionic polymeric sublayer, the low pH of the third composition helping to lower the overall charge of the first anionic polymer and therefore to weaken the interaction between the first anionic polymer and the first cationic polymer inside the first polymeric layer.

The fourth portion of the hair may be the same as the first common area.

The fourth composition may be applied all over the hair.

Step B) may be carried out immediately after step a) or at least 1 hour after step a) or at least 24 hours after step a) or at least 10 days after step a) or at least one month after step a).

Alternatively, the method may further comprise between steps A) and B) the step a) of carrying out the following sequence of steps:
  $a_1$) applying a fourth composition comprising one or more second cationic polymer(s) to a fourth portion of the hair; and
  $a_2$) applying a fifth composition comprising one or more second anionic polymer(s) to a fifth portion of the hair;
  wherein the fourth and the fifth portions of the hair have at least one second common area.

The fifth composition is applied after the fourth composition to the hair.

Having at least one second common area between the fourth portion of the hair to which the fourth composition is applied and the fifth portion of the hair to which the fifth composition is applied ensures that at least a portion of the fifth composition is applied to the same portion of the hair as at least a portion of the fourth composition.

The fourth and the fifth portions of the hair may be the same.

The fourth and/or the fifth compositions may be applied all over the hair.

The method may further comprise between steps A) and B) the optional step b) of repeating step a) at least once, wherein the second common area of each of the repeated steps a) has at least one third common area with the second common area of step a) and the second common area of each of the other repeated steps a), in case step a) is repeated more than once. This ensures that at least a portion of each of the fourth and fifth compositions which are applied to the hair in each of the sequences of steps is applied to the same portion of the hair.

In step a) and/or in at least one of the repeated steps a), the second cationic polymer(s) are cationic coloured polymers and/or the second anionic polymer(s) are anionic coloured polymers.

The first and the second common areas have at least one common area and/or the first and the third common areas have at least one common area.

Having at least one common area between the first and the second common areas and/or between the first and the third common areas ensures that the fourth and the fifth compositions are successively applied to the same portion of the hair wherein the first polymeric layer is obtained. While not wishing to be bound by theory it is believed that this also ensures that the third composition is also applied to the portion of the hair comprising the first polymeric layer and the coloured layer(s) on top of it and therefore helps to remove at least a part of the first polymeric layer and at least the part of the coloured layer(s) which is obtained on top of the part of the first polymeric layer that is removed. While not wishing to be bound by theory, it is believed that the part of the first polymeric layer that is removed is a part of the anionic polymeric sublayer, the low pH of the third composition helping to lower the overall charge of the first anionic polymer and therefore to weaken the interaction between the first anionic polymer and the first cationic polymer inside the first polymeric layer.

The first and the second common areas may be the same and/or the first and the third common areas may be the same.

Step B) may be carried out immediately after step a) or b) or at least 1 hour after step a) or b) or at least 24 hours after step a) or b) or at least 10 days after step a) or b) or at least one month after step a) or b).

Each of the fourth compositions of step a) and of the repeated steps a) may be the same or different. Each of the fifth compositions of step a) and of the repeated steps a) may be the same or different.

In step a) and/or in each of the repeated step a), the fourth and the fifth compositions may be applied all over the hair.

In step b), step a) may be repeated at least at least twice, alternatively at least three times. Alternatively, in step b), step a) may be repeated from 1 to 3 times.

Having a hair colouring step as stated hereinbefore is particularly advantageous. Indeed, by carrying out this hair colouring step, it is possible to provide the hair with the desired colour result and colour intensity in an easy manner. The method is unique in that in each of the sequence of steps a fifth composition comprising one or more second anionic polymer(s) is applied to the hair after a fourth composition comprising one or more second cationic polymer(s) has been applied to the hair.

Since the cationic polymer(s) and the anionic polymer(s) which are comprised in respectively the fourth composition and the fifth composition are high molecular weight molecules, they usually do not diffuse into the hair or at least only to a limited extent when compared with dyes used in standard oxidative hair colouring methods. They usually form polymeric layers on hair which are placed on top of each other by alternating the deposition of the cationic polymers and the anionic polymer(s). By performing the sequence of steps of the hair colouring step more than once it is possible to obtain more than two polymeric layers on hair and therefore to have a better control on the final colour result and colour intensity which is obtained. By increasing the number of layers which are applied to the hair it is possible to obtain hair colorations having increased colour intensity. The user may decide on how many times the sequence of steps should be repeated and therefore have a better control over the colour result which is obtained on hair.

Furthermore, it is particularly advantageous to apply a fifth composition comprising one or more second anionic polymer(s) to the hair after having applied a fourth composition comprising one or more second cationic polymer(s). Indeed, the polymer(s) which are comprised in the fifth composition are negatively charged and therefore the outer layer of the coated hair has an electrostatic structure which is similar to the one of the outer layer of natural hair. Therefore it is possible to apply standard cationic conditioners to the hair after this hair coloring step.

It is particularly important for the hair colouring step to have an anionic polymeric layer which is positioned on top of the cationic polymeric layer. Indeed, the presence of the anionic layer is essential in order to have the possibility of applying a subsequent cationic layer on top of it when the sequence of steps of the hair colouring step is carried out more than once. While not wishing to be bound by theory it is also believed that in some embodiments, the anionic polymeric layer may act as a protective layer for the cationic coloured layer which is placed underneath and therefore may contribute to the good washfastness of the hair coloration.

Furthermore, the compositions which are used in the hair colouring step are particularly advantageous since contrary to standard oxidative hair colouring compositions, these compositions are typically low odour compositions.

In the embodiments wherein in step b) of the hair colouring step, step a) is repeated once, the fourth composition of step a) may comprise one or more second cationic coloured polymer(s) and the fourth composition of the repeated step a) may comprise one or more second cationic uncoloured polymer(s).

The hair colouring step may further comprise step c) of applying after step a) a sixth composition comprising one or more third cationic polymer(s) to a sixth portion of the hair wherein the sixth portion of the hair has at least one common area with the second common area of step a).

Alternatively, the method may further comprise the step d) of applying after step b) a sixth composition comprising one or more third cationic polymer(s) to a sixth portion of the hair, wherein the sixth portion of the hair has at least one common area with the third common area of step b).

In steps c) and/or d), the sixth composition may be applied all over the hair. The third cationic polymer(s) comprised in the sixth composition may be cationic coloured polymers or cationic uncoloured polymers. The third cationic polymer(s) may be selected from the same groups of polymers as described hereinafter for the second cationic polymer(s).

By having a cationic polymeric layer on top of the anionic layer it is possible to provide the user with a good hair feeling which is similar to what is obtained when standard commercially available conditioners are applied to the hair.

Steps $a_1$) and/or $a_2$) of the sequence of steps of the hair colouring step may further comprise the subsequent sub-step of removing the excess of respectively the fourth composition and/or the fifth composition from the hair.

Steps $a_1$) and/or $a_2$) of the sequence of steps of the method may further comprise the subsequent sub-step of applying energy to the hair in the form of heat, ultrasounds, infrared and/or microwaves. This sub-step may be carried out either after the application of the fourth or fifth composition to the hair or after removing the excess of the fourth composition or the fifth composition from the hair. While not wishing to be bound by theory, it is believed that applying energy to the hair may accelerate the speed of formation of the polymeric layers on the hair and therefore may increase the stability of the layers once they are formed on the hair. The hair may be heated to a temperature ranging from 5° C. to 70° C., alternatively 20° C. to 60° C., alternatively 40° C. to 60° C.

Steps $a_1$) and/or $a_2$) of the sequence of steps of the method may further comprise the subsequent sub-step of washing and/or rinsing the hair. The hair may be washed and/or rinsed with a liquid selected from the group consisting of a cosmetically acceptable solvent, a solution comprising a cosmetically acceptable solvent and a cosmetically acceptable salt, a shampoo composition and mixtures thereof. Alternatively, the hair may be washed and/or rinsed with water.

After carrying out the method according to the present invention, a conditioning agent may be applied to the hair. Any of the conditioning agents disclosed hereinafter may be applied to the hair.

Fourth Composition
Pigment(s)

As described hereinbefore, the fourth composition may comprise one or more pigment(s). The pigments are coloured pigments which impart colour effects to the product mass or to the hair, or they may be lustre effect pigments which impart desirable and aesthetically pleasing lustre effects to the composition or to the keratin fibres.

The fourth composition may comprise pigments having a $D_{50}$ particle diameter of from 1 nm to 60 micron. Particle diameter is represented by $D_{50}$, which is the median diameter by volume. $D_{50}$ is measured with a Malvern Mastersizer 2000, which is a laser diffraction particle sizer and it is measured according to ISO 13320:2009(en) with Hydro 2000G or Hydro 2000S where the dispersant is water or ethanol. Detection range is from 0.02 micron to 2000 micron. $D_{50}$ is expressed as $x_{50}$ in ISO 13320:2009(en). Laser diffraction measures particle size distributions by measuring the angular variation in intensity of light scattered as a laser beam passes through a dispersed particulate sample analyser and the particle size is reported as a volume equivalent sphere diameter. A discussion of calculating $D_{50}$ is provided in Barber et al, Pharmaceutical Development and Technology, 3(2), 153-161 (1998), which is incorporated herein by reference.

The fourth composition may comprise pigments having a $D_{50}$ particle diameter of from 100 nm to 20 micron. The pigments may be present in the composition in undissolved form. The fourth composition may comprise a total amount of pigments ranging from 0.01% to 25%, or from 0.1% to 20%, or from 1% to 15%, or from 4% to 10% by total weight of the composition. The pigments are colorants which are virtually insoluble in the composition, and may be inorganic or organic. Inorganic-organic mixed pigments are also possible. The fourth composition may comprise inorganic pigments. The advantage of inorganic pigments is their excellent resistance to light, weather and temperature. The inorganic pigments may be of natural origin, and are, for example, derived from material selected from the group consisting of chalk, ochre, umber, green earth, burnt sienna, and graphite. The pigments may be white pigments, such as, for example, titanium dioxide or zinc oxide, or are black pigments, such as, for example, iron oxide black, or are coloured pigments, such as, for example, ultramarine or iron oxide red, lustre pigments, metal effect pigments, pearlescent pigments, and fluorescent or phosphorescent pigments. Alternatively, the pigments may be coloured, non-white pigments. The pigments may be selected from the group consisting of metal oxides, hydroxides and oxide hydrates, mixed phase pigments, sulfur-containing silicates, metal sulfides, complex metal cyanides, metal sulfates, chromates and molybdates, and the metals themselves (bronze pigments). The pigments may be selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminium sulfosilicates, CI 77007, Pigment Blue 29), chromium oxide hydrate (CI 77289), Prussian blue (ferric ferrocyanide, CI 77510), carmine (cochineal), and mixtures thereof.

The pigments may be pearlescent and coloured pigments based on mica which are coated with a metal oxide or a metal oxychloride, such as titanium dioxide or bismuth oxychloride, and optionally further colour-imparting substances, such as iron oxides, Prussian blue, ultramarine, and carmine. The colour exhibited by the pigment can be adjusted by varying the layer thickness. Such pigments are sold, for example, under the trade names Rona®, Colorona®, Dichrona®, RonaFlair®, Ronastar®, Xirona® and Timiron® all of which are available from Merck, Darmstadt, Germany. For example, Xirona® is a brand for colour travel pigments that display colour shifting effects depending on the viewing angle and are based on either natural mica, $SiO_2$ or calcium aluminium borosilicate flakes, coated with varying layers of $TiO_2$. Pigments from the line KTZ® from Kobo Products, Inc., 3474 So. Clinton Ave., So. Plainfield, USA, are also useful herein, in particular the Surface Treated KTZ® Pearlescent Pigments from Kobo. Particularly useful are KTZ® FINE WHITE (mica and $TiO_2$) having a $D_{50}$ particle diameter of 5 to 25 micron and also KTZ® CELESTIAL LUSTER (mica and $TiO_2$, 10 to 60 micron) as well as KTZ® CLASSIC WHITE (mica and $TiO_2$, 10 to 60 micron). Also useful are SynCrystal Sapphire from Eckart Effect Pigments, which is a blue powder comprising platelets of synthetic fluorphlogopite coated with titanium dioxide, ferric ferrocyanide and small amounts of tin oxide. Also useful is SYNCRYSTAL Almond also from Eckart, which is a beige powder with a copper reflection colour and is composed of platelets of synthetic fluorphlogopite and coated with titanium dioxide and iron oxides. Also useful is Duocrome® RV 524C from BASF, which provides a two colour look via a lustrous red powder with a violet reflection powder due to its composition of mica, titanium dioxide and carmine.

The pigments may be organic pigments. The organic pigments may be selected from the group consisting of natural pigments sepia, gamboge, bone charcoal, Cassel brown, indigo, chlorophyll and other plant pigments. The synthetic organic pigments may be selected from the group consisting of azo pigments, anthraquinoids, indigoids, dioxazine, quinacridone, phthalocyanine, isoindolinone, perylene and perinone, metal complex, alkali blue, diketopyrrolopyrrole pigments, and combinations thereof.

The pigments may be selected from the group consisting of iron oxide, titanium dioxide, mica, borosilicate, and combinations thereof. The pigments may comprise an iron oxide ($Fe_2O_3$) pigment. The pigment may comprise a combination of mica and titanium dioxide.

Second Cationic Polymer(s)

As explained hereinbefore, the fourth composition may comprise one or more second cationic polymer(s). The second cationic polymer(s) may be selected from the group consisting of cationic coloured polymers, cationic uncoloured polymers and mixtures thereof. The second cationic polymer(s) may be strong cation polymer(s) or weak cationic polymer(s). According to an embodiment, the second cationic polymer(s) are weak cationic polymer(s).

Each of the second cationic polymers which are comprised in each of the fourth compositions of step a) and of the repeated steps a) may be the same or different.

In step a) and/or in each of the repeated steps a), the second cationic polymer(s) may be cationic coloured polymers.

The second cationic polymer(s) according to the present invention may comprise one or more monomer unit(s) comprising one or more amino functional group(s). The amino functional group(s) may be selected from the group consisting of primary, secondary, tertiary, quaternary amino functional groups and mixtures thereof. The amino functional group(s) may preferably be selected from the group consisting of primary, secondary amino functional groups and mixtures thereof.

The second cationic polymer(s) may have a charge density at full protonation of at least 0.3, preferably at least 0.6, more preferably at least 0.8, even more preferably at least 1.0 positive charges per monomer unit.

The second cationic polymer(s) may have a weight average molecular weight of more than 0.5 kD, preferably from 0.5 kD to 5000 kD, more preferably from 2 kD to 1000 kD, even more preferably from 10 kD to 200 kD, most preferably from 25 kD to 70 kD.

The second cationic polymer(s) may be selected from the group consisting of polyethyleneimine, polyallylamine hydrochloride, polydiallyldimethylammonium chloride, polyvinylamine, copolymers thereof and mixtures thereof.

The copolymers may be random or block copolymers.

The second cationic polymer(s) may be linear or branched.

The second cationic polymer(s) may be selected from the group consisting of:
a) Linear polyethyleneimine of the formula:

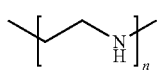

in which n is an integer representing the degree of polymerization, wherein n ranges from 50 to 20,000, alternatively from 100 to 3,500;
b) Branched polyethyleneimine consisting of primary, secondary and tertiary amine groups of the formula:

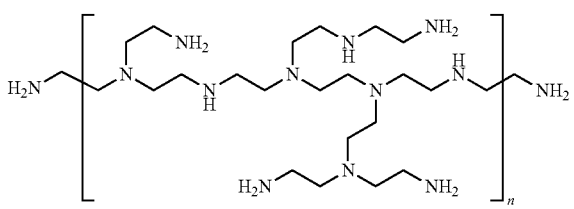

in which n is an integer representing the degree of polymerization, wherein n ranges from 5 to 4,000, alternatively from 50 to 500;
c) Polyallylamine hydrochloride (PAH) of the formula:

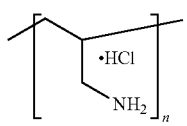

in which n is an integer representing the degree of polymerization, wherein n ranges from 50 to 20,000, alternatively from 150 to 2000;
d) Polydiallyldimethylammonium chloride (PDADMAC) of the formula:

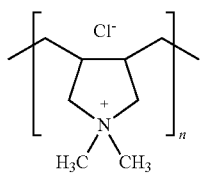

in which n is an integer representing the degree of polymerization, wherein n ranges from 10 to 20,000, alternatively from 150 to 4,000; and
e) copolymers thereof and mixtures thereof.

The copolymers may be random or block copolymers.

The fourth composition may be the same composition as the first composition. The fourth composition may comprise the same cationic polymers as the ones comprised in the first composition.

Fifth Composition

Second Anionic Polymer(s)

The second anionic polymer(s) which are comprised in the fifth composition may be selected from the group consisting of anionic coloured polymers, anionic uncoloured polymers and mixtures thereof.

According to an embodiment, the second anionic polymer(s) is/are weak anionic polymer(s) as described above. The second anionic polymer(s) may also be strong anionic polymer(s). It is sufficient when at least the first anionic polymer(s) is/are weak anionic poylmer(s). The removal of the coloration is improved when also the second anionic polymer(s) are weak anionic polymers. According to an embodiment, the first and the second anionic polymer(s) are weak anionic polymer(s) to further improve the capability of the polymer layer structure to be at least partially removable when the third composition having a low pH value is applied.

Each of the second anionic polymer(s) which are comprised in each of the fifth compositions of step a) and of the repeated steps a) may be the same or different.

In step a) and/or in each of the repeated steps a), the second anionic polymer(s) may be anionic coloured polymers.

The second anionic polymer(s) may have a charge density at full deprotonation of at least 0.3, preferably at least 0.6, more preferably at least 0.8, even more preferably at least 1.0 negative charges per monomer unit.

The second anionic polymer(s) may have a weight average molecular weight of at least 1 kD, preferably from 10 kD to 1000 kD, more preferably from 70 kD to 500 kD.

The second anionic polymer(s) may comprise one or more monomer unit(s) comprising one or more functional group(s) selected from the group consisting of sulfate, sulfonate, carboxylate, phosphate, phosphonate groups and mixtures thereof. The functional group(s) may preferably be selected from the group consisting of sulfate, sulfonate, carboxylate groups and mixtures thereof.

The second anionic polymer(s) may be selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof. The salts may be sodium salts.

The copolymers may be random or block copolymers.

The second anionic polymer(s) may be selected from the group consisting of:

a) Polystyrene sulfonate (PSS) sodium salt of the formula:

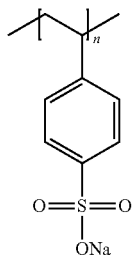

in which n is an integer representing the degree of polymerization, wherein n ranges from 50 to 20,000, alternatively from 150 to 2500;

b) Co-polymer of polystyrene sulfonate (PSS) sodium salt and poly(4-styrenesulfonic acid-co-maleic acid) of the formula:

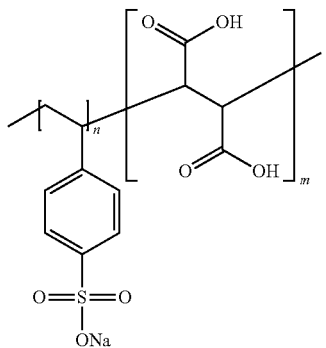

in which n and m are integers representing the degree of polymerization, wherein n+m ranges from 50 to 20,000, alternatively from 150 to 2500;

c) λ-Carrageenan;

d) Dextran sulfate sodium salt;

e) Polyacrylic acid (PAA) of the formula:

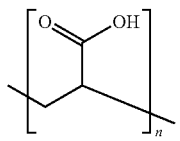

in which n is an integer representing the degree of polymerization, wherein n ranges from 50 to 20,000, alternatively from 150 to 5000;

f) Alginic acid sodium salt;

g) Carboxymethylcellulose sodium salt of the formula:

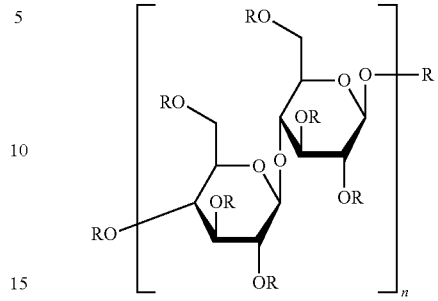

in which:

R is H or $(CH_2)_2COONa$ and n is an integer representing the degree of polymerization; and h) copolymers thereof and mixtures thereof.

The copolymers may be random or block copolymers.

The fifth composition may be the same as the second composition. The fifth composition may comprise the same anionic polymers as the ones comprised in the second composition.

Cationic Coloured Polymers and Anionic Coloured Polymers

The cationic coloured polymers and the anionic coloured polymers used in the present invention comprise at least one chromophore and/or at least one fluorophore. Any of the hereinbefore exemplified cationic polymers or anionic polymers can comprise at least one chromophore and/or at least one fluorophore either in the skeleton or as pendent group.

The chromophores may be selected from the group consisting of nitrobenzene, azo, imine, hydrazine, phenothiazine, xanthene, phenanthridine, phthalocyanin and triarylmethane-based dyes, derivatives thereof, derivatives obtained from direct dyes containing a carbonyl group and mixtures thereof. The chromophores may be selected from the group consisting of acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes, derivatives thereof and mixtures thereof.

The chromophores may be substituted with at least one amine, hydroxyl, sulfate, sulfonate, carboxylate, phosphate, phosphonate, or halide group. These chromophores may be selected from the group consisting of derivatives of acidic nitro direct dyes, acidic azo dyes, acidic azine dyes, acidic triarylmethane dyes, acidic indoamine dyes and non-quinone acidic natural dyes, and mixtures thereof.

The chromophores may also be selected from derivatives of any of the direct dyes exemplified in the direct dyes section of this application.

The fluorophores may be selected from the group consisting of radicals derived from di-, tetra- or hexa-sulfonated triazine-stilbenes, coumarins, imidazolines, diazoles, triazoles, benzoxazolines, biphenyl-stilbenes optical brighteners, and mixtures thereof.

A cationic coloured polymer or an anionic coloured polymer may comprise the same type of chromophore and/or fluorophore or different types of chromophores and/or fluorophores. Having a cationic coloured polymer or an anionic coloured polymer with different types of chromophores and/or fluorophores may help to cover a broad range of colour shades which can be obtained on hair which are coloured according to the method of the present wherein the first composition or the second composition comprises such a cationic coloured polymer or such an anionic coloured polymer.

The cationic coloured polymers may be selected from the group consisting of:

i. Coloured linear or branched polyethyleneimine (PEI) of the formula:

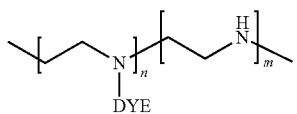

in which n and m are integers representing the degree of polymerization, wherein m/n ranges from 0 to 1,000 provided that n is different from 0 and/or m+n ranges from 50 to 20,000, alternatively from 100 to 3,500;

ii. Coloured polyallylamine of the formula:

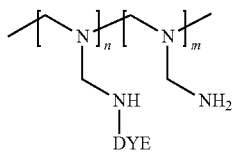

in which n and m are integers representing the degree of polymerization, wherein m/n ranges from 0 to 1,000 provided that n is different from 0 and/or m+n ranges from 50 to 20,000, alternatively from 150 to 2000;

iii. Coloured polydiallyldimethylammonium chloride of the formula:

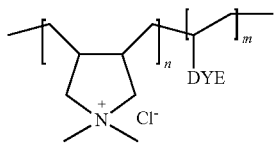

in which n and m are integers representing the degree of polymerization, wherein m/n ranges from 0 to 1,000 provided that n is different from 0 and/or m+n ranges from 10 to 20,000, alternatively from 100 to 4000;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

The cationic coloured polymers may be selected from linear polyethyleneimine (PEI)—Rhodamine B of the formula:

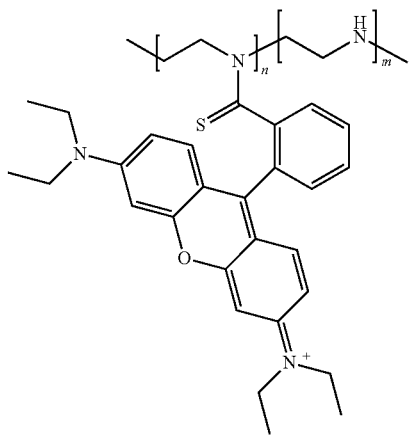

in which n and m are integers representing the degree of polymerization, wherein m/n may range from 0 to 1,000 provided that n is different from 0 and/or m+n may range from 50 to 20,000, alternatively from 100 to 3,500. These polymers may be block copolymers or random copolymers.

The anionic coloured polymers may be selected from anionic coloured polymers with the following formula:

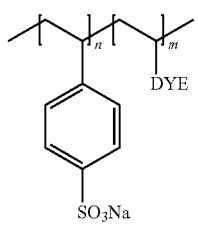

in which n and m are integers representing the degree of polymerization, wherein m/n may range from 0 to 1,000 provided that n is different from 0 and/or m+n may range from 50 to 20,000, alternatively from 150 to 500;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

First to Sixth Compositions

Solvents

The first to sixth compositions which are used to carry out the method according the present invention may further comprise at least one solvent. The solvent may be selected from water, or a mixture of water and at least one organic solvent to dissolve the compounds that would not typically be sufficiently soluble in water. The first to sixth compositions may be aqueous solutions.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

Typically, the compositions may comprise water as a main ingredient, particularly in a total amount ranging from at least 50%, alternatively from at least 60%, alternatively from at least 70%, by total weight of the composition. Typically, when present, the compositions comprise a total amount of organic solvents ranging from about 1% to about 30%, by total weight of the composition.

Concentrations

The first and/or the fourth composition may comprise a total concentration of cationic polymers which is ranging from 0.1 g/L to 100 g/L, alternatively from 0.5 g/L to 100 g/L, alternatively from 2 g/L to 50 g/L, alternatively from 5 g/L to 10 g/L.

The second and/or the fifth composition may comprise a total concentration of anionic polymers which is ranging from 0.1 g/L to 100 g/L, alternatively from 0.5 g/L to 100 g/L, alternatively from 2 g/L to 50 g/L, alternatively from 5 g/L to 10 g/L.

Salt

The first to sixth composition, for example particularly the first and/or the second composition, may comprise a cosmetically acceptable salt at a concentration ranging from 0 to 1.5 mol/L, alternatively from 0.05 to 1 mol/L, alternatively from 0.2 to 0.5 mol/L. The first and/or the second composition may comprise the same cosmetically acceptable salt(s) or different cosmetically acceptable salt(s).

In preferred embodiments, the first composition may comprise a cosmetically acceptable salt at a concentration that is higher than the concentration of the cosmetically acceptable salt in the second composition. Alternatively, the first composition may comprise a cosmetically acceptable salt at a concentration that is lower than the concentration of the cosmetically acceptable salt in the second composition. Alternatively, the first composition may comprise a cosmetically acceptable salt at a concentration that is equal to the concentration of the cosmetically acceptable salt in the second composition.

The cosmetically acceptable salt may be selected from the group consisting of an organic salt, a mineral salt and mixture thereof. The organic salt may be sodium citrate. The mineral salt may be selected from the group consisting of sodium chloride, ammonium sulfate, magnesium chloride, calcium chloride and mixtures thereof. The cosmetically acceptable salt may be sodium chloride.

Adjusting the concentration of the cosmetically acceptable salt in the first composition is another important parameter. For instance, using higher concentrations of cosmetically acceptable salts in the first composition comprising the cationic coloured polymer (e.g. up to 1 mol/L) has the effect that a greater number of negatively charged ions can gather around each cationic polymer chain. This leads to the formation of a strong electrostatic shield around each polymer chain. The resulting decrease of positive charge in the immediate surroundings of each polymer chain has the effect that only those parts of the polymer chain which have still enough positive charge will ionically bind to the negatively charged hair surface. The number decrease of anchoring sites of each polymer chain results in an undulated orientation of each cationic coloured polymer, e.g., on the hair surface, thereby enabling the binding of a greater number of cationic coloured polymers. The greater the number of bound cationic coloured polymers on a defined hair surface portion, the more intensive the colour of this portion. Thus, adjusting the salt concentration, particularly in the first composition, may be particularly useful to modify the colour intensity.

Applicators

The first to sixth compositions may be applied to the hair using an applicator such as a brush or a sponge. Alternatively, the first to sixth composition may be applied to the hair by spraying or foaming the first to sixth composition to the hair or by dipping the hair into the first to sixth composition. Alternatively, the first to sixth composition may be applied to the hair using printing technology.

Hair Colouring Kit

The present invention also relates to a kit for treating hair comprising a first component comprising the first composition as defined hereinbefore, a second component comprising the second composition as defined hereinbefore and a third component comprising the third composition as defined hereinbefore. The kit may further comprise a fourth component comprising the fourth composition as defined hereinbefore and/or a fifth component comprising the fifth composition as defined hereinbefore.

Other Ingredients

The first to sixth compositions according to the present invention may comprise, in addition to the ingredients indicated above, further ingredients in order to further enhance the properties of the composition, as long as these are not excluded by the claims.

Suitable further ingredients include, but not limited to: alkalizing agents; oxidative dye precursors, direct dyes; chelants; radical scavengers; pH modifiers and buffering agents; thickeners and/or rheology modifiers; carbonate ion sources; peroxymonocarbonate ion sources; surfactants; polymers; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Alkalizing Agents

The first, second and fourth to sixth compositions according to the present invention may further comprise at least one alkalizing agent. Any alkalizing agent known in the art may be used.

Typically, the first, second and fourth to sixth compositions may comprise a total amount of alkalizing agents ranging from 0.1% to 10%, alternatively from 0.5% to 6%, alternatively from 1% to 4%, by total weight of the composition.

Alternatively, the first, second and fourth to sixth compositions may comprise a total amount of alkalizing agents of less than 1%, preferably less than 0.5%, more preferably less than 0.3%, even more preferably less than 0.1% by total weight of the composition. The first, second and fourth to sixth compositions compositions may most preferably be free of alkalizing agents. Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine.

The first, second and fourth to sixth compositions may comprise a total amount of ammonia of less than 1%, preferably less than 0.5%, more preferably less than 0.3%, even more preferably less than 0.1% by total weight of the composition. The first, second and fourth to sixth compositions may most preferably be free of ammonia. These embodiments are particularly interesting since such compositions are low odour compositions.

Preferably, if present, the ammonium ions and carbonate ions are present in the composition at a weight ratio of from 3:1 to 1:10, alternatively from 2:1 to 1:5.

When the compositions of the present invention is obtained by mixing a developer and a tint composition prior to use, the alkalizing agent is generally present in the tint composition.

Oxidative Dye Precursors

The first to sixth compositions according to the present invention may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the first to sixth compositions may comprise a total amount of oxidative dye precursors ranging up to 12%, preferably from 0.1% to 10%, more preferably from 0.3% to 8%, even more preferably from 0.5% to 6%, by total weight of the composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the compositions of the invention are obtained by mixing a tint composition and a developer composition, the primary intermediates and couplers are usually incorporated into the tint composition.

Direct Dyes

The first to sixth compositions according to the present invention may further comprise compatible direct dyes, in an amount sufficient to provide additional colouring, particularly with regard to intensity. Typically, the first to sixth compositions may comprise a total amount of direct dyes ranging from about 0.05% to about 4%, by total weight of the composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the compositions are obtained by mixing a tint composition and a developer composition, the direct dyes are usually incorporated into the tint composition.

Chelants

The first to sixth compositions according to the present invention may further comprise at least one chelant (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

Typically, the first to sixth compositions may comprise a total amount of chelants ranging from at least 0.01%, preferably from 0.01% to 5%, more preferably from 0.25% to 3%, even more preferably from 0.5% to 1%, by total weight of the composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof, alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—$PO_3H_2$) or its derivative—$PO_3R_2$, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the composition comprises a chelant selected from the group consisting of diethylenetriamine-N,N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the compositions of the invention are obtained by mixing a tint composition and a developer composition, the chelants may be incorporated in the tint composition and/or in the developer composition. A chelant is usually present in the developer composition for stability reason.

Radical Scavengers

The first to sixth compositions according to the present invention may further comprise at least one radical scavenger. As used herein the term "radical scavenger" refers to a species that can react with a radical, preferably a carbonate radical to convert the radical species by a series of fast reactions to a less reactive species. In one embodiment, the radical scavenger is different from the alkalising agent and/or is present in an amount sufficient to reduce the damage to the hair during the colouring/bleaching process.

Typically, the first to sixth compositions may comprise a total amount of radical scavengers ranging from 0.1% to 10%, preferably from 1% by weight to 7%, by total weight of the composition.

Suitable radical scavengers include, but are not limited to: alkanolamines, amino sugars, amino acids, esters of amino acids, and mixtures thereof alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"—in the context of radical scavengers—means particularly potassium salts, sodium salts, ammonium salts, and mixtures thereof.

pH Modifiers and Buffering Agents

The first to sixth compositions according to the present invention may further comprise, in addition to the alkalizing agent discussed above, a pH modifier and/or buffering agent.

Suitable pH modifiers and/or buffering agents include, but are not limited to: ammonia; alkanolamines (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

According to an embodiment, the pH value of the first composition comprising one or more first cationic polymer(s) may be higher than the pH value of the fourth composition comprising one or more second cationic polymer(s), wherein the second cationic polymer(s) is or are cationic coloured polymer(s). A higher pH value of the first composition may increase the polymer loading of the hair with the one or more first cationic polymer(s) as described further below. This is beneficial as it may also increase the polymer loading of the hair with the one or more first anionic polymer(s) when applying the second composition. A pH value of the fourth composition lower than the pH value of the first composition may prevent undesired weakening of the electrostatic interaction between the polymeric sublayers. The pH value of the first composition may be made deliberately higher than the pH value of any other composition that includes cationic polymers.

If prior to applying the fourth composition comprising one or more second cationic polymer(s), wherein the second cationic polymer(s) is or are cationic coloured polymer(s), step A) is repeated, the pH value for the first composition of each of the repeated steps may be lower than the pH value of the very first composition. Hence, the very first composition may have a higher value than any of the first compositions of the repeated steps A).

According to an embodiment, the difference between the pH value of the first composition and the pH value of the fourth composition may be at least 0.5, particularly at least 1, more particularly at least 1.5, and even more particularly at least 2.

According to an embodiment, the difference between the pH value of the first composition and the pH value of the fourth composition may be equal to or less than 4, particularly equal to or less than 3.5, more particularly equal to or less than 3, and even more particularly equal to or less than 2.5.

According to an embodiment, the pH value of the third composition may be lower than the pH value of the second composition comprising one or more first anionic polymer(s). According to an embodiment, the difference between the pH value of the third composition and the pH value of the second composition may be at least 0.5, particularly at least 1, more particularly at least 1.5, and even more particularly at least 2.

According to an embodiment, the pH value of the third composition may be lower than the pH value of the second composition, which in turn may be lower than the pH value of the fourth composition.

According to an embodiment, the pH value of the fourth composition, which may include one or more second cationic coloured polymer(s), may be less than 9, particularly less than 8.5, more particularly less than 8, even more particularly less than 7.5, and even further particularly less than 7. Without wishing to be tight by theory, applying the fourth composition at a lower pH value than the compositions, such as the first composition, for applying one or more cationic uncoloured polymer(s) may prevent that the one or more cationic coloured polymer(s) enter cuticles of the hair or other pores of the hair. This improves the capability of the polymeric layer system to be decolourized by applying the third composition.

Thickeners and/or Rheology Modifiers

The first to sixth compositions according to the invention may further comprise at least one thickener in an amount sufficient to provide the compositions with a viscosity so that it can be readily applied to the hair without unduly dripping off the hair and causing mess.

Typically, the first to sixth compositions may comprise a total amount of thickeners ranging from at least 0.1%, preferably at least 0.5%, more preferably at least 1%, by total weight of the composition.

Suitable thickeners include, but are not limited to: associative polymers, polysaccharides, non-associative polycarboxylic polymers, and mixtures thereof.

Carbonate Ion Sources

The first to sixth compositions according to the present invention may further comprise at least one source of carbonate ions, carbamate ions, hydrogen carbonate ions, and mixtures thereof in a sufficient amount to reduce damage to the hair during the colouring process.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof alternatively sodium hydrogen carbonate, potassium hydrogen carbonate, and mixtures thereof alternatively ammonium carbonate, ammonium hydrogen carbonate, and mixtures thereof.

Conditioning Agents

The first to sixth compositions according to the present invention may further comprise at least one conditioning agent, and/or be used in combination with a composition comprising at least one conditioning agent.

Typically, the first to sixth compositions may comprise a total amount of conditioning agents ranging from 0.05% to 20%, preferably from 0.1% to 15%, more preferably from 0.2% to 10%, even more preferably from 0.2% to 2%, most preferably from 0.5% to 2%, by total weight of the composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Surfactants

The first, second, fourth, fifth or sixth composition according to the present invention may further comprise one or more surfactant(s).

Typically, the first, second, fourth, fifth or sixth composition may comprise a total amount of surfactants ranging from 0.1% to 30%, preferably from 2% to 30%, more preferably from 8% to 25%, even more preferably from 10% to 20%, by total weight of the composition.

The first, second, fourth, fifth or sixth composition may comprise one or more surfactant(s) selected from the group consisting of anionic surfactants, amphoteric surfactants, nonionic surfactants and mixtures thereof. The first, second, fourth, fifth or sixth composition may comprise a total amount of anionic surfactants ranging from 0.1% to 20%, preferably from 0.1% to 15%, more preferably from 5% to 15%, by total weight of the compositions; and a total amount of amphoteric and/or nonionic components, which may range independently from each other from 0.1% to 15%, preferably from 0.5% to 10%, more preferably from 1% to 8%, by total weight of the compositions.

Ionic Strength

The first to sixth compositions of the present invention may further have an ionic strength as defined herein of less than 1.35 mole/kg, preferably from 0.10 to 0.75 mole/kg, more preferably from 0.20 to 0.60 mole/kg. Whilst not being bound by theory, it is believed that the ionic strength value may also affect the resultant viscosity and root adhesion properties of the composition. The ionic strength can be affected by salt resources such as the dyes, sodium sulphate, ammonium carbonate anti-oxidants and chelants such as EDDS. The dye tends to have the greatest effect on the ionic strength and thus the amounts added in order to provide any particular shade need to be considered in terms of ionic strength as well as dye outcome in order to prevent viscosity and root adhesion problems.

The ionic strength of the compositions is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength.

For example the ionic strength of a mixed 0.050 M $Na_2SO_4$ and 0.020 M NaCl solution is: I=½((2×(+1)²× 0.050)+(+1)²×0.020+(−2)²×0.050+(−1)²×0.020)=0.17 M.

Foam

The first to sixth compositions of the invention may be provided in the form of foam which is applied to the hair. Foam formation is typically achieved by the use of a foaming agent incorporated within the composition in combination with a manually operated foaming device. Such manually operated foaming devices are known in the art and include aerosols devices, squeeze foamers and pump foamers.

Suitable foaming agents includes surfactants such as anionic, nonionic and amphoteric surfactants, nonionic surfactants being preferred; polysaccharides; polyvinyl pyrrolidone and copolymers thereof acrylic polymers such as Acrylates copolymer (Aculyn 33) and Acrylates/Steareth-20 methacrylates (Aculyn 22); C12-C24 fatty acids such as stearates and mixtures thereof.

Molecular Weight

According to an embodiment, the one or more first cationic polymer(s) of the first composition may have a higher molecular weight than the one or more second cationic polymer(s) of the fourth composition. Using a higher molecular weight may allow the formation of a thicker and/or denser polymeric sublayer which may be beneficial for the following layers and also for the removal of the coloured layers. Furthermore, using a higher molecular weight for the one or more first cationic polymer(s) may also reduce the risk that one or more first cationic polymer(s) may be replaced by cationic coloured polymer(s).

The molecular weight is expressed as weight average molecular weight.

According to an embodiment, the fourth composition comprising one or more second cationic polymer(s) being cationic coloured polymer(s) and/or the fifth composition comprising one or more second anionic polymer(s) being anionic coloured polymer(s) is/are substantially free from low molecular weight compounds selected from the group consisting of coloured polymer(s), coloured monomer(s), unbound chromophore(s), and fluorophore(s), and mixtures thereof. According to an embodiment, "low molecular weight compounds" are compounds having a molecular weight of less than 500 Da, particularly less than 1 kDa, more particularly less than 2 kDa, even more particularly less than 3 kDa, and further more particularly less than 5 kDa. According to an embodiment, "substantially free" may mean less than 1000 ppm, particularly less than 500 ppm, more particularly less than 100 ppm, and even more particularly less than 50 ppm. The monomers mentioned above mean the monomeric units from which the polymers are made. 1 ppm corresponds to 1 µg/kg polymer.

According to an embodiment, the molecular weight distribution of the cationic coloured polymer(s) and/or of the anionic coloured polymer(s) may be substantially free from low molecular weight polymeric compounds as described above. Such a molecular weight distribution may be obtained by suitable purification steps such as dialysis or filtration.

Avoiding low molecular weight compounds that includes chromophores and/or fluorophores may avoid that such low molecular weight compounds diffuse through the polymeric layer, which may be uncoloured, and interact with the hair. Such low molecular weight compounds may then remain on the hair even after the third composition has been applied.

According to an embodiment, the molecular weight for the coloured polymers may be in the ranges as described further above in connection with the fourth and fifth composition, or may also have a lower limit of 15 kDa, particularly of 25 kDa, and more particularly of 40 kDa, and an upper limit of 300 kDa, particularly 200 kDa, and more particularly 150 kDa. Specific examples are 25 kDa to 300 kDa, 25 kDa to 150 kDa, 40 kDa to 200 kDa, 40 kDa to 150 kDa, and 70 kDa to 150 kDa, without being limited thereto.

Modifications of a Method for Treating Hair

According to an embodiment, the invention also relates to a method for treating hair, wherein the method includes:

B1) applying a composition having a pH of less than 7, particularly less than 6, more particularly less than 5, partially or completely to a polymeric layer system formed on the hair, the polymeric layer system comprising:

one or more first cationic polymer(s) on a first portion of the hair; and one or more first anionic polymer(s) on a second portion of the hair, the first anionic polymer(s) being weak anionic polymer(s);

wherein the first and second portions have at least one first common area.

Step B1) may correspond to the above described step B) and the composition of step B1) may correspond to the third composition of step B). The composition may have a pH ranging from 1 to 7, particularly from 1 to 6, particularly from 1 to 5.5, more particularly from 1.5 to 5.5, even more particularly from 1.5 to 5, and further more particularly from 1.5 to 4.5.

Broadly speaking, the approach described herein is directed to a method for disintegrating or at least partially removing of a polymeric layer system provided on keratin fibres of the hair that includes, or is formed of, at least one or more cationic polymer(s) and one or more anionic polymer(s). The one or more cationic polymer(s) may form a cationic polymeric sublayer of a polymeric layer of the polymeric layer system and the one or more anionic polymer(s) may form an anionic polymeric sublayer of the polymeric layer of the polymeric layer system. The polymeric layer system may include at least one polymeric layer having a cationic polymeric sublayer and an anionic polymeric sublayer. The polymeric layer may be uncoloured, i.e. each of the sublayers are uncoloured. The polymeric layer system may also include, in addition to the polymeric layer, at least one cationic coloured layer and/or at least one anionic coloured layer so that the polymeric layer system includes at least one uncoloured polymeric base layer, which can include one or more sublayers, and at least one coloured polymeric layers, which can include at least one or more coloured sublayers and optionally at least one uncoloured sublayer. The polymeric layer system may also include, in addition to the uncoloured polymeric layer a further uncoloured polymeric layer having a cationic uncoloured polymeric sublayer and an anionic uncoloured polymeric sublayer. At least one cationic coloured layer and/or at least one anionic coloured layer can be on the further uncoloured polymeric layer.

According to an embodiment, the invention also relates to a method for treating hair, wherein the method includes:

B1) applying a composition having a pH of less than 7, particularly less than 6, more particularly less than 5, at least to a polymeric layer on a hair, the polymeric layer system comprising:

a cationic polymeric sublayer comprising one or more first cationic polymer(s) on a first portion of the hair; and an anionic polymeric sublayer comprising one or more first anionic polymer(s) on a second portion of the hair, the first anionic polymer(s) being weak anionic polymer(s);

wherein the first and second portions have at least one first common area.

The polymeric layer system may include the first polymeric layer as described further above. The polymeric layer system may be formed by step A) including steps i) and ii) as described further above. The polymeric layer system may also be formed by other methods and is not limited to the above described step A) including steps i) and ii). The formation of the polymeric layer system is optional as long as there is a polymeric layer system provided on the hair that includes the first one or more cationic polymer(s) and the first one or more anionic polymer(s). The composition of step B1), or the third composition of step B), acts on the thus provided polymeric layer system which results in an at least partial or complete disintegration or removal of the polymeric layer system, for example at least of the first one or more anionic polymer(s) or the anionic polymeric sublayer.

The polymeric layer system on the hair may also include one or more second cationic polymer(s) and/or one or more pigment(s), particularly one or more second cationic polymer(s), on a fourth portion of the hair, wherein the fourth portion of the hair has at least one common area with the first common area, and wherein the second cationic polymer(s) are cationic coloured polymers. The second cationic polymer(s) may be cationic coloured polymers as described above.

Broadly speaking, the method is directed to a partial or complete removal of the polymeric layer system and of optional further layers which are part of the polymeric layer system. In an embodiment, the composition of step B1), or the third composition of step B), may be applied to an area of the hair, or to the full hair, where the one or more first cationic polymer(s) and the one or more first anionic polymer(s) form together a polymeric layer, or the first polymeric layer, of the polymeric layer system. As described above, it is believed that the (first) composition weakens the interaction between the first anionic polymer(s) and the first cationic polymer(s) inside the polymeric layer system and therefore may help to remove a part of the polymeric layer system, i.e. the anionic polymeric sublayer and/or any further cationic polymeric sublayer on the first anionic polymer(s). Since the interaction between the anionic polymeric sublayer and any cationic polymeric layer on the anionic polymeric sublayer also weakens, the cationic polymeric layer on the anionic polymeric sublayer may also be also removed from the hair. If, for example, the cationic polymeric layer on the anionic polymeric sublayer is a cationic coloured polymeric layer, this coloured layer is removed so that the hair becomes uncoloured.

In a more broad approach, the composition of step B1) may be applied to an area of the hair, or to the full hair, where at least the one or more first cationic polymer(s), which may be uncoloured, and the at least one or more first anionic polymer(s), which may be coloured, form together the polymeric layer system. The first anionic coloured polymer(s) are released or removed by the decrease of the pH caused by applying the composition as described above.

The composition of step B1) may also be applied to an area of the hair, or to the full hair, where the one or more first cationic polymer(s), which may be uncoloured, and the one or more first anionic polymer(s), which may also be uncoloured, form together a polymeric layer, or the above described first polymeric layer, of the polymeric layer system. One or more second cationic polymer(s), which may be coloured, can be formed on the first polymeric layer to form a cationic coloured polymeric sublayer. When applying the composition of step B1), or the third composition of step B), to the polymeric layer system that includes the first polymeric layer and the second cationic coloured polymeric sublayer on the first polymeric layer, the interaction between the respective polymeric sublayers are believed to be weaken by the low pH leading to a disintegration of the layer arrangement and release at least of the cationic coloured polymeric sublayer.

According to an embodiment, the composition of step B1), or the third composition of step B), may also be applied to an area of the hair, or to the full hair, where a polymeric layer system is formed which includes the first polymeric layer, which includes the cationic polymeric sublayer and the anionic polymeric sublayer, and a second polymeric layer, which includes a second cationic polymeric sublayer and a second anionic polymeric sublayer, wherein the second polymeric layer is formed on the first polymeric layer. At least one or both of the second cationic polymeric sublayer and the second anionic polymeric sublayer may be coloured polymeric sublayers.

In view of the above, the composition of step B1), or the third composition of step B), is used for decolouring hair that was previously coloured by a polymeric layer, or polymeric layers, having at least a coloured polymeric sublayer such as a cationic coloured polymeric sublayer and/or an anionic coloured polymeric sublayer. The invention thus also includes use of the composition of step B1), or the first composition of step B), for decolouring hair.

The invention also pertains to a composition, such as a composition useful for removing a polymeric hair colouration from hair. The composition may be suitable for removing coloured polymeric sublayers of the polymeric hair colouration which includes at least a cationic polymeric sublayer and an anionic polymeric sublayer on the cationic polymeric sublayer, and optionally a further cationic polymeric sublayer on the anionic polymeric sublayer. The further cationic polymeric sublayer may be a cationic coloured polymeric sublayer as described above. The composition has a pH value of less than 7, particularly less than 6, and may have a pH ranging from 1 to 6, particularly from 1 to 5.5, more particularly from 1.5 to 5.5, even more particularly from 1.5 to 5, and further more particularly from 1.5 to 4.5. The composition may further include one or more cationic surfactant(s) and/or anionic surfactant(s) and/or one or more oxidizing agent(s) as described above.

The composition may further include pH modifier and/or buffering agents as described above.

The composition may further include a thickener and/or rheology modifiers as described above.

The composition may further include a solvent as described above.

The composition may further include a salt as described above.

The composition may further include chelants as described above.

According to an embodiment, the composition useful for removing a polymeric hair colouration may be substantially free of the cationic and/or anionic polymers of the first, second, fourth, fifth and sixth composition.

Improved Polymer Loading of First Polymeric Layer

According to an embodiment, the first composition may have a first pH value, the second composition may have a second pH value, the third composition may have a third pH value, and the fourth composition may have a fourth pH value. The pH values can be different from each other.

According to an embodiment, the first composition comprising one or more first cationic polymer(s) has a first pH value higher than fourth pH value of the fourth composition comprising one or more second cationic polymer(s) and/or one or more pigment(s). Without wishing to be tight by theory, it is believed that a higher pH value renders the first cationic polymer(s) less charged resulting in an increased loading of the hair surface with the first cationic polymer(s). The cationic polymeric sublayer of the first polymeric layer can thus be provided with a higher polymer loading. This also improves the binding, and loading, of the subsequently formed anionic polymeric sublayer.

The fourth pH of the fourth composition may be lower than the first pH value of the first composition to avoid that a high pH weakens the interaction between the previously formed polymeric sublayers bound to keratin fibres of the hair. However, since the polymer loading of the cationic polymeric sublayer of the first polymeric layer is increased as described above, the anionic polymeric sublayer also shows an increased loading which facilitates binding of the second cationic polymer(s).

For example, the first composition may have a pH value (first pH value) higher than 8, particularly higher than 8.5, more particularly higher than 9, and even more particularly higher than 9.5. The first composition may have a pH value less than 13, particularly less than 12, more particularly less than 11, and even more particularly less than 10.5. An example is a pH in a range from 8 to 13, particularly from 8.5 to 12 or 8 to 11, more particularly from 8.5 to 11 or 9 to 11, and even more particularly from 9 to 10.5.

The fourth composition may have a pH value (fourth pH value) less than 9.5, particularly less than 9, more particularly less than 8.5, and even more particularly less than 8.

According to an embodiment, the difference of the pH values (first and fourth pH values) of the first composition and the fourth composition can be at least 0.5, particularly at least 1, and more particularly at least 1.5.

The pH of the second composition may be higher than the pH of the third composition to avoid that a too low pH of the second composition weakens the interaction between previously formed polymeric sublayers bound to keratin fibres of the hair. However, since the polymer loading of the cationic polymeric sublayer of the first polymeric layer is increased as described above, the anionic polymeric sublayer also shows an increased loading which facilitates binding of the second cationic polymer(s).

The second cationic polymer(s) of the fourth composition may be coloured while the first cationic polymer(s) of the first composition may be uncoloured.

In addition to that, the second composition comprising one or more first anionic polymer(s) may have a pH value (second pH value) lower than the first composition. At the lower pH, it is believed that the first cationic polymer(s) linked to the hair are highly charged thus presenting more charges to the first anionic layer polymer(s) so that the anionic polymeric sublayer is strongly bound and has a higher loading.

According to an embodiment, the first pH value can be higher than the second pH value.

According to an embodiment, the fourth pH value can be lower than the first pH value.

According to an embodiment, the one or more second anionic coloured polymer(s) of the fifth composition may include an anionic polymer backbone and at least one cationic chromophore and/or cationic fluorophore linked to the anionic polymer backbone. The overall charge of the second anionic coloured polymer(s) is such that the second anionic coloured polymer(s) is anionic at the pH of the fifth composition. Having the second anionic coloured polymer(s) provided with cationic groups by linking the cationic chromophores and/or cationic fluorophores further facilitates removal of the second anionic coloured polymer(s) by applying the third composition. Due to the cationic groups of the chromophore and/or fluorophores the second anionic coloured polymer(s) may become neutral or even inversely charged when the third composition is applied which improves removal of the second cationic coloured polymer(s).

The same also applies to anionic coloured polymer(s) of other compositions which may be subsequently applied. Hence, the invention may include a polymeric layer structure on keratin fibres of the hair having one or more first cationic uncoloured polymer(s), one or more first anionic uncoloured polymer(s), one or more second cationic coloured polymer(s), and one or more second anionic coloured polymer(s), wherein the one or more second anionic coloured polymer(s) includes a anionic polymer backbone and at least one cationic chromophore and/or cationic fluorophore linked to the anionic polymer backbone. Such a polymeric structure has an improved decolouration capability, i.e. disintegration or removal capability, when applying a composition having a low pH value such as the composition of step B1) or the first composition of step B).

The invention may include a polymeric layer structure on keratin fibres of the hair having one or more first cationic uncoloured polymer(s), one or more first anionic uncoloured polymer(s), and one or more second anionic coloured polymer(s), wherein the one or more second anionic coloured polymer(s) includes an anionic polymer backbone and at least one cationic chromophore and/or cationic fluorophore linked to the anionic polymer backbone. Such a polymeric structure has an improved decolouration capability, i.e. disintegration or removal capability, when applying a composition having a low pH value such as the composition of step B1) or the first composition of step B).

The composition of step B1) or the first composition of step B) may therefore be particularly used for decolouration of the polymeric layer structure having at least one or more cationic coloured polymer(s) which includes a cationic polymer backbone and at least one anionic chromophore and/or anionic fluorophore linked to the cationic polymer backbone and/or one or more anionic coloured polymer(s), which includes an anionic polymer backbone and at least one cationic chromophore and/or cationic fluorophore linked to the anionic polymer backbone.

The polymeric structure to which the composition of step B1), or the first composition of step B), can beneficially be applied for decolouration may also include two polymeric layers each including one or more first cationic uncoloured polymer(s) and one or more first anionic uncoloured polymer(s), and at least one or more second cationic coloured polymer(s) and/or one or more second anionic coloured polymer(s) on the two polymeric layers.

In view of the above, the invention includes the exemplary embodiments (1) to (24) as defined below:

(1) A method for treating hair comprising:
  A) carrying out the following sequence of steps:
    i) applying a first composition comprising one or more first cationic polymer(s) to a first portion of the hair; and
    ii) applying a second composition comprising one or more first anionic polymer(s) to a second portion of the hair; and
  B) applying a third composition having a pH of less than 7, particularly less than 6 to a third portion of hair,
  wherein the first, second and third portions have at least one first common area and
  wherein the first anionic polymer(s) are weak anionic polymers.

(2) The method according to exemplary embodiment (1), wherein the third composition has a pH ranging from 1 to 7, particularly from 1 to 6, more particularly from 1 to 5.5, more particularly from 2 to 6, even more particularly from 1.5 to 5, and further more particularly from 1.5 to 4.5.

(3) The method according to any of the preceding claims, wherein the first cationic polymer(s) comprise one or more amino functional group(s) per polymer chain, wherein the amino functional group(s) are selected from the group consisting of primary, secondary, tertiary amino functional groups and mixtures thereof.

(4) The method according to any of the preceding exemplary embodiments, wherein the first cationic polymer(s) are selected from the group consisting of polyethyleneimine, polyallylamine hydrochloride, polyvinylamine, copolymers thereof and mixtures thereof, preferably from the group consisting of polyethyleneimine, copolymers thereof and mixtures thereof.

(5) The method according to any of the preceding exemplary embodiments, wherein the first anionic polymer(s) are selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, carboxydextrane salts, copolymers thereof and mixtures thereof, preferably from the group consisting of polyacrylic acid salts, poly(methacrylic acid) salts, alginic acid salts, carboxymethylcellulose salts, carboxydextrane salts, copolymers thereof and mixtures thereof.

(6) The method according to any of the preceding exemplary embodiments, wherein at least one of steps i), ii) or B), preferably all the steps i), ii) or B) further comprises the subsequent sub-step of:
  washing and/or rinsing the hair, preferably with a liquid selected from the group consisting of a cosmetically acceptable solvent, a solution comprising a cosmetically acceptable solvent and a cosmetically acceptable salt, a shampoo composition and mixtures thereof, more preferably with water.

(7) The method according to any of the preceding exemplary embodiments, wherein:
  the first composition comprises a total concentration of cationic polymers ranging from 0.1 g/L to 100 g/L, preferably from 0.5 g/L to 100 g/L, more preferably from 2 g/L to 50 g/L, even more preferably from 5 g/L to 10 g/L and/or
  the second composition comprises a total concentration of anionic polymers ranging from 0.1 g/L to 100 g/L, preferably from 0.5 g/L to 100 g/L, more preferably from 2 g/L to 50 g/L, even more preferably from 5 g/L to 10 g/L.

(8) The method according to any of the preceding exemplary embodiments, wherein the method comprises between steps A) and B):
  a) applying a fourth composition comprising one or more second cationic polymer(s) and/or one or more pigment(s), preferably one or more second cationic polymer(s) to a fourth portion of the hair,
  wherein:
    the fourth portion of the hair has at least one common area with the first common area and
    the second cationic polymer(s) are cationic coloured polymers.

(9) The method according to any of the preceding exemplary embodiments, wherein the method comprises between steps A) and B):
  a) carrying out the following sequence of steps:
    a1) applying a fourth composition comprising one or more second cationic polymer(s) to a fourth portion of the hair; and
    a2) applying a fifth composition comprising one or more second anionic polymer(s) to a fifth portion of the hair;

the fourth and the fifth portions of the hair having at least one second common area;
and optionally
b) repeating step a) at least once, wherein the second common area of each of the repeated steps a) has at least one third common area with:
the second common area of step a); and
the second common area of each of the other repeated steps a) in case step a) is repeated more than once;
wherein in step a) and/or in at least one of the repeated steps a), the second cationic polymer(s) are cationic coloured polymers and/or the second anionic polymer(s) are anionic coloured polymers, and
wherein:
the first and the second common areas have at least one common area and/or
the first and the third common areas have at least one common area.
(10) The method according to any of exemplary embodiment (8) or (9), wherein the second cationic polymer(s) comprises one or more monomer unit(s) comprising one or more amino functional group(s), preferably wherein the amino functional group(s) are selected from the group consisting of primary, secondary, tertiary, quaternary amino functional groups and mixtures thereof, more preferably wherein the amino functional group(s) are selected from the group consisting of primary, secondary amino functional groups and mixtures thereof.
(11) The method according to any of exemplary embodiments (8) to (10), wherein the second cationic polymer(s) are selected from the group consisting of linear or branched polyethyleneimine, polyallylamine hydrochloride, polydiallyldimethylammonium chloride, copolymers thereof and mixtures thereof.
(12) The method according to any of exemplary embodiments (9) to (11), wherein the second anionic polymer(s) comprise one or more monomer unit(s) comprising one or more functional group(s) selected from the group consisting of sulfate, sulfonate, carboxylate, phosphate, phosphonate groups and mixtures thereof, preferably from the group consisting of sulfate, sulfonate, carboxylate groups and mixtures thereof.
(13) The method according to any of exemplary embodiments (9) to (12), wherein the second anionic polymer(s) are selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof.
(14) The method according to any of the previous exemplary embodiments, wherein the first composition has a pH value larger than the fourth composition.
(15) The method according to exemplary embodiment (14), wherein the first composition has a pH value equal to or larger than 8, particularly equal to or larger than 8.5, and more particularly equal to or larger than 9, and wherein the fourth composition has a pH value equal to or less than 8, particularly equal to or less than 7.5, and more particularly equal to or less than 7.
(16) The method according to any of the previous exemplary embodiments, wherein the third composition has a pH value equal to or lower than the first composition.
(17) The method according to any of the previous exemplary embodiments, wherein the third composition has a pH value equal to or lower than the second composition.
(18) The method according to any of the previous exemplary embodiments, wherein the fourth composition comprising one or more second cationic polymer(s) being cationic coloured polymer(s) and/or the fifth composition comprising one or more second anionic polymer(s) being anionic coloured polymer(s) is/are substantially free from low molecular weight compounds selected from the group consisting of coloured polymer(s), coloured monomer(s), unbound chromophore(s), and fluorophore(s), and mixtures thereof.
(19) A kit for treating hair comprising:
a first component comprising the first composition as defined in any of exemplary embodiments (1) to (18),
a second component comprising the second composition as defined in any of exemplary embodiments (1) to (18),
a third component comprising the third composition as defined in any of exemplary embodiments (1) to (18).
(20) Kit according to exemplary embodiment (19), wherein the third composition has a pH value equal to or lower than the second composition.
(21) Kit according to exemplary embodiment (19) or (20), further comprising a fourth component comprising a fourth composition as defined in any of exemplary embodiments (1) to (18).
(22) Kit according to exemplary embodiment (21), wherein the first composition has a pH value larger than the fourth composition.
(23) A method for treating hair, comprising:
B1) applying a composition having a pH of less than 7, particularly less than 6, partially or completely, to a polymeric layer system formed on the hair, the polymeric layer system comprising:
one or more first cationic polymer(s) on a first portion of the hair; and
one or more first anionic polymer(s) on a second portion of the hair, the first anionic polymer(s) being weak anionic polymer(s);
wherein the first and second portions have at least one first common area.
(24) A method according to exemplary embodiment (23), wherein the polymeric layer system formed on the third portion of the hair further comprises at least one of:
one or more second cationic coloured polymer(s) on a fourth portion of the hair; and
one or more second anionic coloured polymer(s) on a fifth portion of the hair;
wherein the fourth and fifth portions have at least one second common area; and
wherein the first and the second common areas have at least one common area.
(25) Use of a component comprising the third composition as defined in any of the exemplary embodiments (1) to (18), or of the third composition of step B) of exemplary embodiment (22) or (24), for decolouring hair that is at least partially coloured by a polymeric layer system, or by polymeric layers, formed on keratin fibres of the hair or a portion of the hair, the polymeric layer system, or polymeric layers, comprising at least one coloured polymeric sublayer, such as a cationic coloured polymeric sublayer, and/or an anionic coloured polymeric sublayer.
(26) Use of a component comprising the third composition as defined in any of the exemplary embodiments (1) to (18), or of the third composition of step B) of exemplary embodiment (22) or (24), for removing at least one coloured polymeric sublayer from hair, wherein the at least one coloured polymeric sublayer is a sublayer of a polymeric layer system formed on keratin fibres of the hair or of a portion of the hair, wherein the polymeric layer system formed on the keratin fibres optionally further includes at least one cationic uncoloured polymeric sublayer and/or optionally at least one anionic uncoloured polymeric sublayer.

(27) Use according to exemplary embodiment (24) or (25), wherein the third composition has a pH ranging from 1 to 7, particularly from 1 to 6, particularly from 1 to 5.5, more particularly from 1.5 to 5.5, even more particularly from 1.5 5, and further more particularly from 1.5 to 4.5.

(28) Use according to any of the exemplary embodiments (25) to (27), wherein the third composition further comprises one or more cationic surfactant(s) and/or one or more anionic surfactant(s) and/or one or more oxidizing agent(s).

(29) Use according to any of the exemplary embodiments (25) to (26), wherein the third composition further comprises at least one pH modifier and/or buffering agent.

(30) Composition for decolouring hair, wherein the composition has a pH of equal to or less than 7, particularly equal to or less than 6, particularly a pH ranging from 1 to 6, more particularly from 1 to 5.5, even more particularly from 1.5 to 5.5, further more particularly from 1.5 to 5, and even further more particularly from 1.5 to 4.5.

(31) Composition according to exemplary embodiment (30), wherein the composition further comprises one or more cationic surfactant(s) and/or one or more anionic surfactant(s) and/or one or more oxidizing agent(s).

(32) Composition according to exemplary embodiment (30) or (31), wherein the composition further comprises at least one pH modifier and/or buffering agent.

(33) Use of a composition for decolouring hair that is at least partially coloured by a polymeric layer system, or by polymeric layers, formed on keratin fibres of the hair or a portion of the hair, the polymeric layer system, or polymeric layers, comprising at least one of an anionic coloured polymeric sublayer and an anionic uncoloured polymeric sublayer, and optionally at least one of a cationic coloured polymeric sublayer and a cationic uncoloured polymeric sublayer, wherein at least one of the anionic coloured polymeric sublayer and anionic uncoloured polymeric sublayer comprises a weak anionic polymer having a given pKa value, wherein the composition is selected such that the pH value of the composition is lower than the given pKa value of the weak anionic polymer by at least 1, particularly by at least 1.5, more particularly by at least 2, and even more particularly by at least 2.5.

(34) Use according to exemplary embodiment (33), wherein composition further includes at least one anionic surfactant(s).

EXAMPLES

The following are non-limiting examples of the method of the present invention. The examples are given solely for the purpose of illustration and are not to be construed as limitations of the present invention, as many variations thereof are possible without departing from the spirit and scope of the invention, which would be recognized by one of ordinary skill in the art.

In the following section the solvent used to prepare the different compositions is water, unless otherwise specified.

Synthesis Methods for Obtaining the Cationic Coloured Polymer Used in the Examples:

Cationic Coloured Polymers

Branched polyethyleneimine labeled with Reactive Blue 116 (PEI-Turq.):

Starting materials:
Branched polyethyleneimine (PEI) (LUPASOL G 500), Mw=25,000 Da, available from BASF (CAS: 9002-98-6)
Reactive Blue 116 Drimarene K-2B Turquoise, available from mijn-eigen.nl Synthesis method:

The following method has been used for labeling Branched polyethyleneimine (PEI) with Reactive Blue 116

1) Dissolving 2.5 g of a 40 wt % solution of Branched polyethyleneimine (PEI) in a 40 ml methanol solution containing 2.22 g of Reactive Blue 116;
2) Stirring the suspension at 70° C. overnight;
3) Further stirring the resultant mixture at room temperature for 12 h;
4) Centrifuging the resultant mixture and collecting the supernatant;
5) Adding methanol to the precipitate, centrifuging the mixture and collecting the supernatant;
6) Repeating step 5) until the resulting supernatant is colorless;
7) Mixing all the resulting supernatant solutions from steps 4) to 6);
8) Adding 2.5 ml of a 32 wt % hydrochloric acid solution to the resulting mixture from step 7)
9) Centrifuging the resulting suspension and collecting the precipitate;
10) Washing the precipitate with acetone until the supernatant is colorless;
11) Drying the precipitate and dissolving it in water;
12) Dialyzing the resulting solution against a solution of 0.15 M NaCl and $10^{-4}$ to $10^{-5}$ M HCl
13) Freeze-drying the product Cationic Uncoloured Polymer Used in the Examples
Branched polyethyleneimine (PEI), LUPASOL G 500, Mw=25,000 Da (CAS: 9002-98-6) available from BASF Anionic Uncoloured Polymer Used in the Examples
Poly(methacrylic acid) sodium salt (PMAA), Mw=15,000 Da (CAS: 25087-26-7) available from Polysciences, Inc.
Poly(acrylic) acid sodium salt (PAA), Mw=30,000 Da (CAS: 9003-04-7) available from Aldrich
Alginic acid sodium salt (CAS: 9005-38-3) available from Fluka
Dextran sulfate sodium salt (DxS), Mw=500,000 Da (CAS: 9011-18-1) available from Fluka.

First Set of Experimental Data—Examples of Methods According to the Present Invention wherein Different Types of Third Composition at Different pH have been Used Example 1

| First Composition | |
|---|---|
| Ingredients | g/l |
| PEI | 5.00 (0.5 wt %) |
| NaCl | 11.69 (0.2 mol/l) |

-continued

First Composition

| Ingredients | g/l |
| --- | --- |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

Second or Fifth Composition

| Ingredients | g/l |
| --- | --- |
| PMAA | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

Fourth Composition

| Ingredients | g/l |
| --- | --- |
| PEI-Turquoise | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5%) | pH adjusted to 8 by adding 1.0 mol/l NaOH or 1.0 mol/l HCl

Third Composition

| Ingredients | g/l |
| --- | --- |
| Sodium acetate | 4.10 (0.05 mol/l) | pH was adjusted to 2 by adding 1.0 mol/l NaOH or 1.0 mol/l HCl

Comparative Example 1A

A hair swatch has been treated as in example 1 except that the third composition has been replaced with the following third composition:

Third Composition

| Ingredients | g/l |
| --- | --- |
| Wella ® Brilliance Shampoo | 10 | pH was not adjusted

Comparative Example 1B

A hair swatch has been treated as in example 1 except that the third composition has been replaced with the following third composition:

Third Composition

| Ingredients | g/l |
| --- | --- |
| Na2HPO4 | 7.10 (0.05 mol/l) | pH was adjusted to 11.5 by adding 1.0 mol/l NaOH or 1.0 mol/l HCl

Step 1: Formation of the Polymeric Layer and the coloured Layer on Top of the Polymeric Layer:

A hair swatch has been treated according to the following protocol:

(i) Preparing the first, second, fourth and fifth compositions shortly before application;
(ii) Applying 4 mL of the first composition to the hair swatch with a brush and wrapping the hair swatch with a commercial kitchen plastic wrap;
(iii) Agitating the first composition with the hair swatch in plastic wrap for 15 min at 55° C. in a laboratory-type drying cabinet;
(iv) Rinsing the hair swatch for 30 s with running lukewarm tap water at a temperature of 30° C. to 35° C.;
(v) Applying 4 mL of the second composition to the hair swatch with a brush and wrapping the hair swatch with a commercial kitchen plastic wrap;
(vi) Agitating the second composition with the hair swatch in plastic wrap for 15 min at 55° C. in a laboratory-type drying cabinet;
(vii) Rinsing the hair swatch for 30 s with running lukewarm tap water at a temperature of 30° C. to 35° C.;
(viii) Applying 4 mL of the fourth composition to the hair swatch with a brush and wrapping the hair swatch with a commercial kitchen plastic wrap;
(ix) Agitating the fourth composition with the hair swatch in plastic wrap for 15 min at 55° C. in a laboratory-type drying cabinet;
(x) Rinsing the hair swatch for 30 s with running lukewarm tap water at a temperature of 30° C. to 35° C.;
(xi) Applying 4 mL of the fifth composition to the hair swatch with a brush and wrapping the hair swatch with a commercial kitchen plastic wrap;
(xii) Agitating the fifth composition with the hair swatch in plastic wrap for 15 min at 55° C. in a laboratory-type drying cabinet;
(xiii) Rinsing the hair swatch for 30 s with running lukewarm tap water at a temperature of 30° C. to 35° C.;
(xiv) Drying the hair swatch first with tissue paper and then with a hair dryer.

Step 2: Removal of the Polymeric Layer

The hair swatch obtained at the end of step 1) has been then treated according to the following protocol:

(i) Applying 5 ml of the third composition to the coloured hair swatch with a brush for 30 s in a plastic bowl and letting the hair swatch soaked for 30 s;
(ii) Rinsing the hair swatch for 30 s with running lukewarm tap water at a temperature of 30° C. to 35° C.;
(iii) Drying the hair swatch first with tissue paper and then with a hair dryer.

Second Set of Experimental Data—Examples of Methods According to the Present Invention wherein Different Types of Anionic Polymers have been Used in the Second and Fifth Compositions

Example 2

A hair swatch has been treated as in example 1 except that the second and fifth compositions have been replaced with the following composition:

| Second or Fifth Composition | |
|---|---|
| Ingredients | g/l |
| PAA | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

Comparative Example 2A

A hair swatch has been treated as in example 2 except that the third composition has been replaced with the third composition of the comparative example 1A.

Comparative Example 2B

A hair swatch has been treated as in example 2 except that the third composition has been replaced with the third composition of the comparative example 1B.

Example 3

A hair swatch has been treated as in example 1 except that the second and fifth compositions have been replaced with the following composition:

| Second or Fifth Composition | |
|---|---|
| Ingredients | g/l |
| Alginate | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

Comparative Example 3A

A hair swatch has been treated as in example 3 except that the third composition has been replaced with the third composition of the comparative example 1A.

Comparative Example 3B

A hair swatch has been treated as in example 3 except that the third composition has been replaced with the third composition of the comparative example 1B.

Example 4

A hair swatch has been treated as in example 1 except that the second and fifth compositions have been replaced with the following composition:

| Second or Fifth Composition | |
|---|---|
| Ingredients | g/l |
| DxS | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

Comparative Example 4A

A hair swatch has been treated as in example 4 except that the third composition has been replaced with the third composition of the comparative example 1A.

Comparative Example 4B

A hair swatch has been treated as in example 4 except that the third composition has been replaced with the third composition of the comparative example 1B.

Experimental Results

The experimental results, based on visual assessment, are summarized in the table below, wherein AA means very good, A means good, B means acceptable, and C means not acceptable.

As it becomes apparent from FIG. 1, experiment 1 lead to a removal of the coloured polymeric layer structure to a very good visual result with virtually no colouration left on the hair when using a third composition with pH 2. Experiment 2 gave also good results with some colouration left on the hair. In experiment 3, the colouration left on hair was noticeable but a reduction of coloration was clearly observable. In experiment 4, the colouration virtually did not chance.

The comparative examples 1B, 2B, 3B, 4B using a high pH composition resulted in a virtually complete removal of the colouration as the pH weakens the charge of the cationic polymers.

The stability of the colouration against washing, i.e. the washfastness, was good to very good for all experiments as illustrated by the comparative examples 1A, 1B, 1C, and 1D.

| Example No. | OFF Polyanion | pKa/ Polyanion character | Layers | After Coating | After shampoo (comparative examples A) | Washing with pH 11.5/ Removal strength (comparative examples B) | Washing with pH 2/ Removal strength (Example) |
|---|---|---|---|---|---|---|---|
| 1 | Poly(methacrylic acid) (PMAA) | 5-6 Weak | L1. PEI L2. PMAA L3. PEI-Turq. L4. PMAA | AA | AA | AA | AA |
| 2 | Poly(acrylic acid) (PAA) | 4-5.5 Weak | L1. PEI L2. PAA L3. PEI-Turq. L4. PAA | AA | A | AA | A |

-continued

| Example No. | OFF Polyanion | pKa/ Polyanion character | Layers | After Coating | After shampoo (comparative examples A) | Washing with pH 11.5/ Removal strength (comparative examples B) | Washing with pH 2/ Removal strength (Example) |
|---|---|---|---|---|---|---|---|
| 3 | Alginate (Alg) | 1.5-3.5 Weak to Strong | L1. PEI L2. Alg L3. PEI-Turq. L4. Alg | AA | A | AA | B |
| 4 | Dextran sulfate (DxS) | ~2 Strong | L1. PEI L2. DxS L3. PEI-Turq. L4. DxS | AA | AA | AA | C |

Third Set of Experimental Data—Examples of Methods According to the Present Invention wherein the First Composition Comprises a Cationic Coloured Polymer and wherein Different Acidic Solutions are Used as Third Composition Cationic Coloured Polymers Branched polyethyleneimine labeled with Reactive Red 180 (PEI-Red):

Starting materials:

Branched polyethyleneimine (PEI) (LUPASOL G 500), Mw=25,000 Da, available from BASF (CAS: 9002-98-6)

Reactive Red 180 available from S3 Chemicals (CAS: 72828-03-6).

Synthesis method:

The following method has been used for labeling Branched polyethyleneimine (PEI) with Reactive Red 180 (Red):

1) Dissolving 12.5 g of a 40 wt % solution of Branched polyethyleneimine (PEI) in a 200 ml methanol solution containing 14.05 g of Reactive Red 180;
2) Stirring the suspension at 60° C. for 1 hour;
3) Further stirring the resultant mixture at room temperature for 12 h;
4) Centrifuging the resultant mixture and collecting the supernatant;
5) Adding methanol to the precipitate, centrifuging the mixture and collecting the supernatant;
6) Repeating step 5) until the resulting supernatant is colorless;
7) Mixing all the resulting supernatant solutions from steps 4) to 6);
8) Adding 12.5 ml of a 32 wt % hydrochloric acid solution to the resulting mixture from step 7)
9) Centrifuging the resulting suspension and collecting the precipitate;
10) Washing the precipitate with acetone until the supernatant is colorless;
11) Drying the precipitate and dissolving it in water;
12) Dialyzing the resulting solution against a solution of 0.15 M NaCl and $10^{-4}$ to $10^{-5}$ M HCl
13) Freeze-drying the product Example 5

A long hair swatch has been treated first with a first composition (PEI-Red) and a second composition (DxS).

Removal of the Polymeric Layer

The long hair swatch was cut into separate hair swatches and each was then treated according to the following protocol. The respective third composition is given below in the table:

(i) Immersing the coloured hair swatch in the third composition at room temperature for 10 min;
(ii) Rinsing the hair swatch for 30 s with running lukewarm tap water at a temperature of 30° C. to 35° C.;
(iii) Shampooing the hair swatch;
(iv) Rinsing the hair swatch for 30 s with running lukewarm tap water at a temperature of 30° C. to 35° C.;
(v) Drying the hair swatch.

L*, a*, b* Measurements

The colorimetric parameters in the CIE L* a* b* system have been measured for each of the hair swatches obtained in Example 6 as described in the first set of experimental data.

Results and Conclusions:

The ΔE values obtained for the different examples are summarized in Table 1 below.

TABLE 1

| Example | Sequence of layers prior to removal | Third composition | $\Delta E_{Stage2/Stage1}$[1] | $\Delta E_{Stage3/Stage1}$[2] |
|---|---|---|---|---|
| Example 5A | PEI-Red/DxS | Formic acid, 5% | 22.6 | 19.1 |
| Example 5B | PEI-Red/DxS | Acetic acid, 5% | 22.6 | 20.7 |
| Example 5C | PEI-Red/DxS | Propionic acid, 5% | 22.6 | 21.1 |
| Example 5D | PEI-Red/DxS | Citric acid, 5% | 22.6 | 20.4 |
| Example 5E | PEI-Red/DxS | Oxalic acid, 5% | 22.6 | 20.9 |
| Example 5F | PEI-Red/DxS | Ascorbic acid, 5% | 22.6 | 19.8 |

[1] corresponds to the overall change of colour measured between stage 2 and stage 1
[2] corresponds to the overall change of colour measured between stage 3 and stage 1

As shown above, high pH solutions can be used to at least partially remove a cationic coloured polymeric layer from hair.

Example 6

Single Cationic Coloured Polymeric Layer

A long hair swatch has been treated as in example 5 but only with a first composition containing PEI-Red and not with a second composition. Hence, the polymeric layer system includes only a cationic coloured polymeric layer. The removal procedures is the same as in Example 5.
L*, a*, b* Measurements The colorimetric parameters in the CIE L* a* b* system have been measured for each of the hair swatches obtained in Example 6 as described in the first set of experimental data.
Results and Conclusions:

The ΔE values obtained for the different examples are summarized in Table 1 below.

TABLE 1

| Example | Sequence of layers prior to removal | Third composition | $\Delta E_{Stage2/Stage1}$[1] | $\Delta E_{Stage3/Stage1}$[2] |
|---|---|---|---|---|
| Example 6A | PEI-Red | Formic acid, 5% | 24.2 | 20 |
| Example 6B | PEI-Red | Acetic acid, 5% | 24.2 | 16.7 |
| Example 6C | PEI-Red | Proprionic acid, 5% | 24.2 | 21.2 |
| Example 6D | PEI-Red | Citric acid, 5% | 24.2 | 19.9 |
| Example 6E | PEI-Red | Oxalic acid, 5% | 24.2 | 20.6 |
| Example 6F | PEI-Red | Ascorbic acid, 5% | 24.2 | 20.3 |

[1] corresponds to the overall change of colour measured between stage 2 and stage 1
[2] corresponds to the overall change of colour measured between stage 3 and stage 1

As shown above, low pH solutions can be used to at least partially remove a single cationic coloured polymeric layer from hair. A comparison between Example 5 and Example 6 demonstrates that removing a single cationic coloured polymeric layer (the cationic coloured polymers) from hair with low pH solutions performs better when no additional anionic polymeric layer is present on the cationic coloured polymeric layer.

An uncoloured polymeric base layer, which can include, for example, a cationic uncoloured polymeric layer and an anionic uncoloured polymeric layer, is not needed for removal purposes, but can optionally be formed prior to forming the coloured cationic polymeric layer. For many applications, a partial removal of the cationic coloured polymers is sufficient, for example when the hair is subsequently coloured with another colour. Using an optional uncoloured polymeric base layer further improves the removal of the coloured cationic polymeric layer.

Furthermore, it has been found out that removal of coloured cationic polymers with low pH solutions (third composition) is particularly effective when no uncoloured polymeric double layer is present on the hair beneath the cationic coloured polymeric layer, i.e. when the cationic coloured polymeric layer is the first, and particularly the only, polymeric layer on the hair. An optional anionic polymeric layer can be formed on the cationic coloured polymeric layer.

While not wishing to be bound by theory, it is believed that the low pH of the third composition may help to weaken the interaction between the first cationic polymer(s) and the surface of the hair. It is believed that the effect obtained with low pH solutions during the removal of the cationic coloured polymeric layer is based on charge/discharge interactions with the hair surface. The low pH may result in a reversal of surface charges of the hair, which may result in electrostatic repulsion of the cationic coloured polymeric layer, which remains charged, from the hair surface. A low pH specifically seems to weaken the charge interaction between the surface charges of the hair and the first cationic polymer(s) such as the cationic coloured polymeric layer.

The step of applying a second composition comprising one or more first anionic polymer(s) to the hair is optional, and the method for treating hair, such as for removing coloured cationic polymers from hair, may include:
A) carrying out the following sequence of steps:
  i) applying a first composition comprising one or more first cationic polymer(s), such as coloured cationic polymers, to a first portion of the hair; and
B) applying a third composition having a pH of less than 7, particularly less than 6, more particularly less than 5.5 such as less than 5, to a third portion of hair,
wherein the first and third portions have at least one first common area.

Step A) can optionally include step ii) of applying a second composition comprising one or more first anionic polymer(s), such as uncoloured anionic polymers, to a second portion of the hair. The first anionic polymer(s) can be weak anionic polymers. Step ii) can be omitted.

In view of the above, a method, kit, use, and composition for decolouring hair which is coloured with a polymeric single layer, a polymeric double-layer having two polymeric sublayers, or a polymeric multi-layer having a plurality of polymeric sublayers is disclosed. At least one of the polymeric layers, or sublayers, is coloured. For example, the first cationic polymeric layer, or sublayer, formed by the first cationic polymer can be coloured using a cationic coloured polymer. The first anionic polymer used to form the first anionic polymeric layer, or sublayer, can be coloured or can be uncoloured.

In the broadest sense, at least one of the one, two, three, four or multiple polymeric layers or sublayers is coloured. For example, the first cationic polymeric sublayer is coloured, and the optional first anionic polymeric sublayer is uncoloured. A further example includes a first cationic uncoloured sublayer, a first anionic uncoloured sublayer, a second cationic coloured sublayer, and a second uncoloured, or coloured, anionic sublayer, in this order.

The coloured polymeric layer, such as a cationic coloured polymeric layer, or coloured polymeric sublayers can be removed by applying the third composition having a pH of less than 7, particularly less than 6. The hair that was coloured with the coloured polymeric layer or coloured polymeric sublayer or sublayers is decoloured and appears in its natural colour.

The third composition having a low pH can therefore be used to remove the coloured polymeric layer, the coloured polymeric sublayer of a polymeric double layer, or a coloured polymeric sublayer of a polymeric multi-layer.

The third composition can contain, for example, an organic acid such as a monocarboxylic acid, dicarboxylic acid, a tricarboxylic acid, or a polycarboxylic acid. Examples are citric acid, formic acid, acetic acid, proprionic acid, oxalic acid, and ascorbic acid. Other organic acids can be used as well. The organic acids can be used as pH modifier to adjust the pH of the third composition.

The third composition may include at least one, at least two, or at least three different organic acids. A further option is a combination of an organic acid and an inorganic acid.

CONCLUSION

The amount of colour which is removed is much higher when the first anionic polymer is weaker and therefore demonstrates that it is easier to remove the polymeric layer which is obtained by successively applying the first and the second compositions as well as any coloured layer obtained on top of this polymeric layer when the first anionic polymer is weaker i.e. has a higher pKa value.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:
1. A method for treating hair comprising:
   A) carrying out the following sequence of steps:
      i) applying a first composition comprising a first cationic polymer to a first portion of the hair; wherein the first, cationic polymer is uncolored polyethyleneimine: and
      ii) applying a second composition comprising a first anionic polymer to a second portion of the hair; wherein the first, anionic polymer is uncolored dextran sodium sulfate: and
   B) applying a third composition having a pH ranging from 1 to 7 to a third portion of hair, wherein the first, second and third portions have at least one first common area wherein:
   the first composition comprises a total concentration of cationic polymer ranging from 0.1 g/L to 100 g/L and/or
   the second composition comprises a total concentration of anionic polymer ranging from 0.1 g/L to 100 g/L
   wherein the method comprises between steps A) and B):
   a) carrying out the following sequence of steps:
      $a_1$) applying a fourth composition comprising a second cationic polymer to a fourth portion of the hair, wherein the second cationic polymer is polyethyleneimine with Reactive Red 180 (PEI Red); and
      $a_2$) applying a fifth composition comprising a second anionic polymer to a fifth portion of the hair, wherein the second anionic polymer is uncolored dextran sodium sulfate;
   the fourth and the fifth portions of the hair having at least one second common area; and
   optionally
   b) repeating step a) at least once.

* * * * *